US012746167B2

(12) United States Patent
Vidal

(10) Patent No.: US 12,746,167 B2
(45) Date of Patent: Sep. 29, 2026

(54) SMART DENTAL TREATMENT CHAIR, AND A SYSTEM UTILIZING ARTIFICIAL INTELLIGENCE AND COMPUTERIZED VISION TO MONITOR REAL-TIME PROGRESS OF A DENTAL TREATMENT

(71) Applicant: Natalie Vidal, Jupiter, FL (US)

(72) Inventor: Natalie Vidal, Jupiter, FL (US)

( * ) Notice: Subject to any disclaimer, the term of this patent is extended or adjusted under 35 U.S.C. 154(b) by 247 days.

(21) Appl. No.: 18/661,614

(22) Filed: May 11, 2024

(65) Prior Publication Data

US 2025/0345225 A1 Nov. 13, 2025

(51) Int. Cl.

| | |
|---|---|
| ***A61G 15/10*** | (2006.01) |
| ***A61B 90/00*** | (2016.01) |
| ***A61G 15/14*** | (2006.01) |

(52) U.S. Cl.

CPC .............. *A61G 15/10* (2013.01); *A61B 90/37* (2016.02); *A61G 15/14* (2013.01)

(58) Field of Classification Search

CPC ...................................................... A61G 15/14

See application file for complete search history.

(56) References Cited

U.S. PATENT DOCUMENTS

| | | | | |
|---|---|---|---|---|
| 2017/0071810 | A1* | 3/2017 | Pagano Bringel | G06F 3/041 |
| 2017/0071811 | A1* | 3/2017 | Lazarof | A61C 17/032 |
| 2021/0313052 | A1* | 10/2021 | Makrinich | G06Q 10/06398 |
| 2022/0331047 | A1* | 10/2022 | Shelton, Iv | G06T 19/006 |
| 2025/0366948 | A1* | 12/2025 | Giataganas | A61B 90/361 |

FOREIGN PATENT DOCUMENTS

| | | | | |
|---|---|---|---|---|
| EP | 4353214 a1 | * | 4/2024 | A61G 15/14 |

* cited by examiner

*Primary Examiner* — Eric J Rosen
*Assistant Examiner* — Courtney N Huynh

(57) ABSTRACT

Smart dental treatment chair, and a system utilizing Artificial Intelligence (AI) and computerized vision analysis to dynamically monitor real-time progress of a dental treatment, to dynamically report the progress to the patient, and to provide additional benefits to dental patients. A dental treatment chair includes video cameras that capture real time video, and a microphone that captures sound and speech. Computerized vision unit perform analysis of the video, and a Large Language Model (LLM) performs analysis of text extracted from uttered speech, to determine the current step in a multiple-step dental procedure. A display unit is oriented towards the patient, and displays a dynamically-updated progress bar and percentage value, indicating the actual progress of the ongoing dental treatment. Optionally, the smart dental treatment chair also integrally plays music that the patient selects and controls, sprays an aromatic agent, and provides other benefits to the dental patient.

3 Claims, 5 Drawing Sheets

SMART DENTAL TREATMENT CHAIR, AND A SYSTEM UTILIZING ARTIFICIAL INTELLIGENCE AND COMPUTERIZED VISION TO MONITOR REAL-TIME PROGRESS OF A DENTAL TREATMENT

FIELD

Some embodiments are related to the field of dentistry.

BACKGROUND

A dentist, or a dental surgeon, is a healthcare professional who specializes in dentistry, the branch of medicine focused on the teeth, gums, and mouth. A dentist may work alone, or may be assisted by a supporting team that aids in providing oral health services; for example, a dental assistant, a dental hygienist, a dental technician.

A dental patient, or a dental treatment patient, typically visits a dentist's office or a dentist's clinic, in order to undergo a dental treatment. A variety of dental treatment are performed by dentists worldwide; for example, restorative dental treatment, construction of dental fillings or crowns or bridges, prosthetic treatments (e.g., dentures), endodontic treatments (e.g., root canal), periodontal therapy, teeth extraction, teeth implants, or the like.

SUMMARY

Some embodiments provide a smart dental treatment chair, and a system utilizing Artificial Intelligence (AI) and computerized vision analysis to dynamically monitor (and to report to the patient) real-time progress of a dental treatment, and to provide additional benefits to dental patients. A dental treatment chair includes a plurality of video cameras that capture real time video, and a microphone that captures sound and speech. Computerized vision analysis unit perform analysis of the video, and a Large Language Model (LLM) performs analysis of the text extracted from uttered speech; to determine the current step or the current phase in a multiple-step dental procedure. A display unit is oriented towards the patient, and displays a dynamically-updated progress bar and a percentage value, indicating the actual progress of the dental treatment. Optionally, the smart dental treatment chair also plays music that the patient selects, sprays an aromatic agent, and provides other benefits to the dental patient.

Some embodiments provide other and/or additional benefits and/or advantages.

DETAILED DESCRIPTION OF SOME DEMONSTRATIVE EMBODIMENTS

Figure 1A:
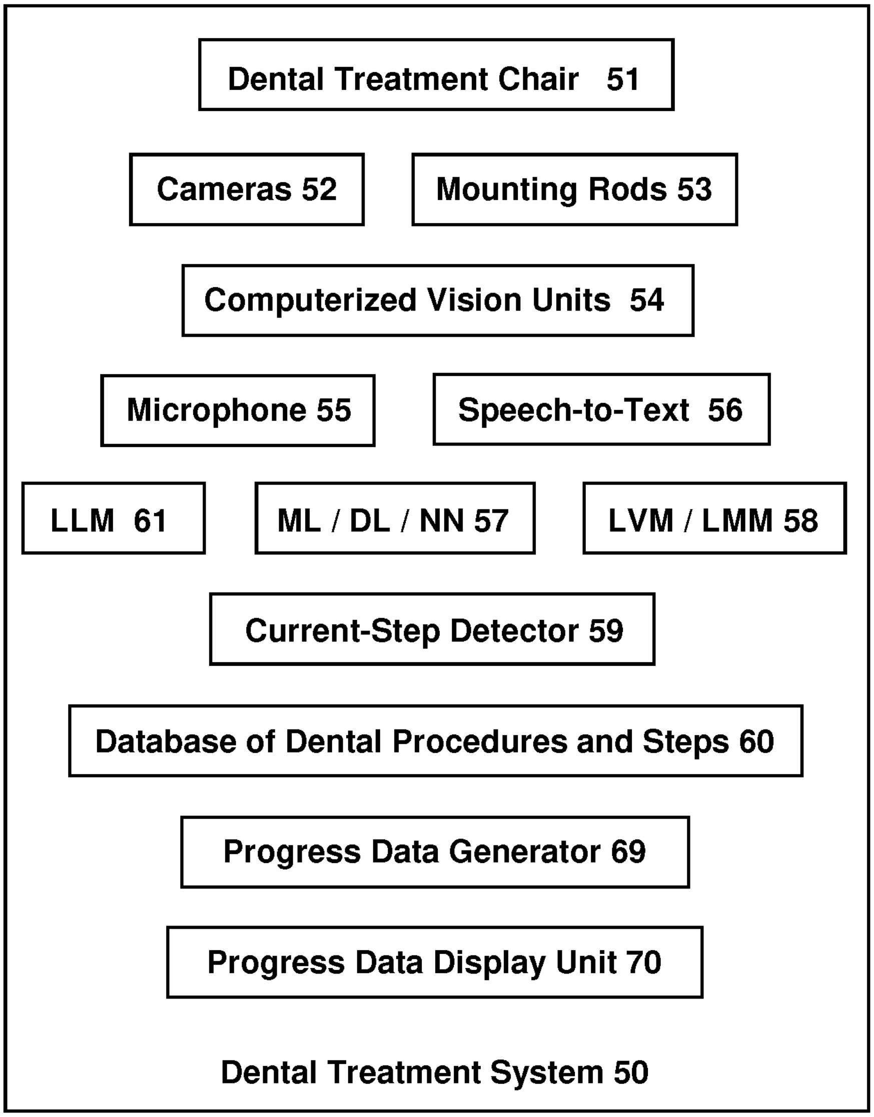
FIG. 1A is a schematic block diagram illustration of a dental treatment system, in accordance with some demonstrative embodiments.

The Applicant has realized that some dental patients may feel anxiety, fear, or helplessness while sitting or laying down on a dental treatment seat at a dentist's office or a dental clinic, and/or while undergoing a dental treatment by a dentist and/or a dental assistant.

Particularly, realized the Applicant, some dental patients do not know at every given moment of the dental treatment: how much time is left until the dental treatment would end; how much time elapsed so far within this dental treatment; and/or, which particular step or phase of a multiple-step dental treatment is currently performed, or was recently completed, or would be provided next or soon.

The Applicant has realized that some dentists do not always fully explain verbally to the patient which step of the dental treatment is currently being done, or is about to be performed. Sometimes the dentist is occupied with performing the dental task or with preparing dental tools or with handling dental tools, or with requesting a dental assistant to prepare certain tasks; and the occupied dentist may not verbalize the progress to the dental patient as often as the patient desires and/or as informatively as the patient desires.

Additionally or alternatively, realized the Applicant, some dentists tend to be more silent and less talkative in their nature, and do not verbally share such information at all, or at a frequency or granularity level that a particular patient may desire.

Additionally or alternatively, realized the Applicant, some dentists do not speak the same natural language that the patient fully understand; for example, a Miami-based dentist is fluent in English, and treats a Miami-based patient who is fluent in Spanish and does not master the English language. Such language barriers may prevent the dental patient from comprehending which particular step of the dental treatment is performed now or was completed recently, or what is the exact progress of the dental treatment being performed.

Additionally or alternatively, realized the Applicant, some disabled dentists and/or disabled patients may not be able to verbally share information. For example, a dentist who is mute, or that has a speech impairment, can perform a superb dental treatment, but may not be able to verbally convey information regarding the progress of the ongoing dental treatment. Similarly, for example, a patient who is deaf or is hearing impaired, may not be able to hear all or some of the information that the dentist conveys verbally; particularly if the dentists speaks in a quiet voice and/or behind a protective mask, and/or if there are ambient noises in the room from dental equipment (e.g., a saliva suction tool that makes suction noises; its associated motor; a dental drill).

The Applicant has realized that dental treatment patients may benefit from having a visual indicator of a Progress Bar, that is visually displayed to the dental patient during the dental treatment session, and that dynamically updates to indicate the progress of the ongoing dental treatment; such as, using a Progress Bar that gradually fills-up or advances from 0 percent of completion to 100 percent of completion, and/or using a Percentage Counter that gradually increases from 0 percent of completion to 100 percent of completion.

The Applicant has further realized that the dentist, and his assistant or team, may not have the time to manually input information (via a keyboard, or via voice dictation) into a computer or other device that would then, in turn, generate such Progress Bar. Rather, realized the Applicant, the dentist is often occupied in performing the dental treatment itself to the best of her ability, focusing on the dental treatment itself and not on conveying to a dictation device or a computer the progress-related information.

Some embodiments of the present invention provide an innovative system and a computerized method, that are configured and trained to automatically and autonomously deduce or detect or sense or recognize the current stage/step/phase of a dental treatment, and that are able to determine or estimate the real-time progress of the dental treatment; using advanced Computerized Visional analysis of real-time video footage that is captured (with the patient's informed consent) via multiple video cameras, and that is analyzed in real-time or in near-real-time by a plurality of hardware processors and/or CPUs and/or GPUs that are specifically trained to visually recognize particular dental events or dental-treatment events or dental-treatment stages. In some embodiments, a Large Language Model (LLM), similar to OpenAI GPT or Meta Llama or Microsoft Copilot or Google Gemini or Claude Sonnet or Mistral or the like, is further utilized to perform LLM-based analysis of text, that is extracted from speech uttered by the dentist and/or the dental assistant(s), and to further deduce (via LLM analysis) from such extracted speech further insights about the currently-performed dental step or the recently-completed dental-step or the soon-upcoming/subsequent dental-step, in a multiple-step dental treatment.

Reference is made to FIG. 1A, which is a schematic block diagram illustration of a system 50, in accordance with some demonstrative embodiments. System 50 may comprise the following components; which are then explained and described in greater detail in conjunction with the subsequent drawings; system 50 may comprise: a Dental Treatment Chair 51, accommodating a dental treatment patient that is being treated by a dentist and a dental assistant; a plurality of video cameras 52, each can be a high resolution 1080p or 4K or 8K video camera; a plurality of corresponding Mounting Rods 53, each rod being movable or adjustable and holding thereon one of the cameras; a plurality of Computerized Vision Units 54, each of them configured to perform real time or near-real-time processing of video and/or video frames captured by one of the cameras and/or by a combination of two or more cameras, and configured to extract from such video particular data and particular insights with regard to the progress of the dental treatment procedure; an Acoustic Microphone 55, configured to capture audio and particularly speech that is uttered by persons in the vicinity of the dental chair; a Speech-to-Text converter 56, that converts such captured speech into text in a natural language (e.g., English, Spanish, or the like); a Large Language Model (LLM) 61, configured to perform LLM analysis of text that corresponds to speech uttered by the dentist and/or dental assistant and/or the dental patient, and particularly configured to deduce from such analyzed speech which step in the dental procedure was recently performed or completed and/or is being performed and/or is about to be performed, and/or configured to deduce other data related to a multi-step dental treatment (e.g., a verbal indication by the dentist that he decided to Skip or Postpone a particular step, or that he is about to Re-do a particular step); a Machine Learning (ML)/Deep Learning (DL)/Neural Network (NN) 57 model or unit, which may be configured to further analyze the data obtained by the LLM and/or by computerized vision analysis, to predict or estimate the next step in the dental treatment (e.g., when the dental assistant is seen in the video footage mixing the filling material, the ML/DL NN unit may predict that the next step is the dental treatment is insertion of the filling material into a tooth cavity within 60 seconds); an LVM/LMM 58 unit, which is a Language and Vision Model or a Large Multi-Modality model, configured to deduce insights with regard to the latest/previous/current/upcoming step in the dental procedure, based on data captured or sensed by two or more different modalities (e.g., video data captured by cameras, and speech/textual data captured by the microphone); a Current-Step Detector 59, which detects or estimates or determines the current step in a multi-step dental procedure, based on the insights deduced by one or more of the previous components; a Database of Dental Procedures and Steps 60, which may store therein pre-defined records indicating the set of steps for dental procedures, and such data may be utilized by the Current-Step Detector 59 and/or by other components (e.g., the LLM, the LVM/LMM, the computerized vision units) to accurately deduce the current/previous/next step in the dental treatment; a Progress Data Generator 69, configured to generate data that enable a hardware processor to command a Progress Data Display Unit 70 to display a representation of the progress of the dental treatment, such as by a progress bar that gradually fills out and/or by a percentage indication in a scale of 0 to 100 percent.

Figure 2:
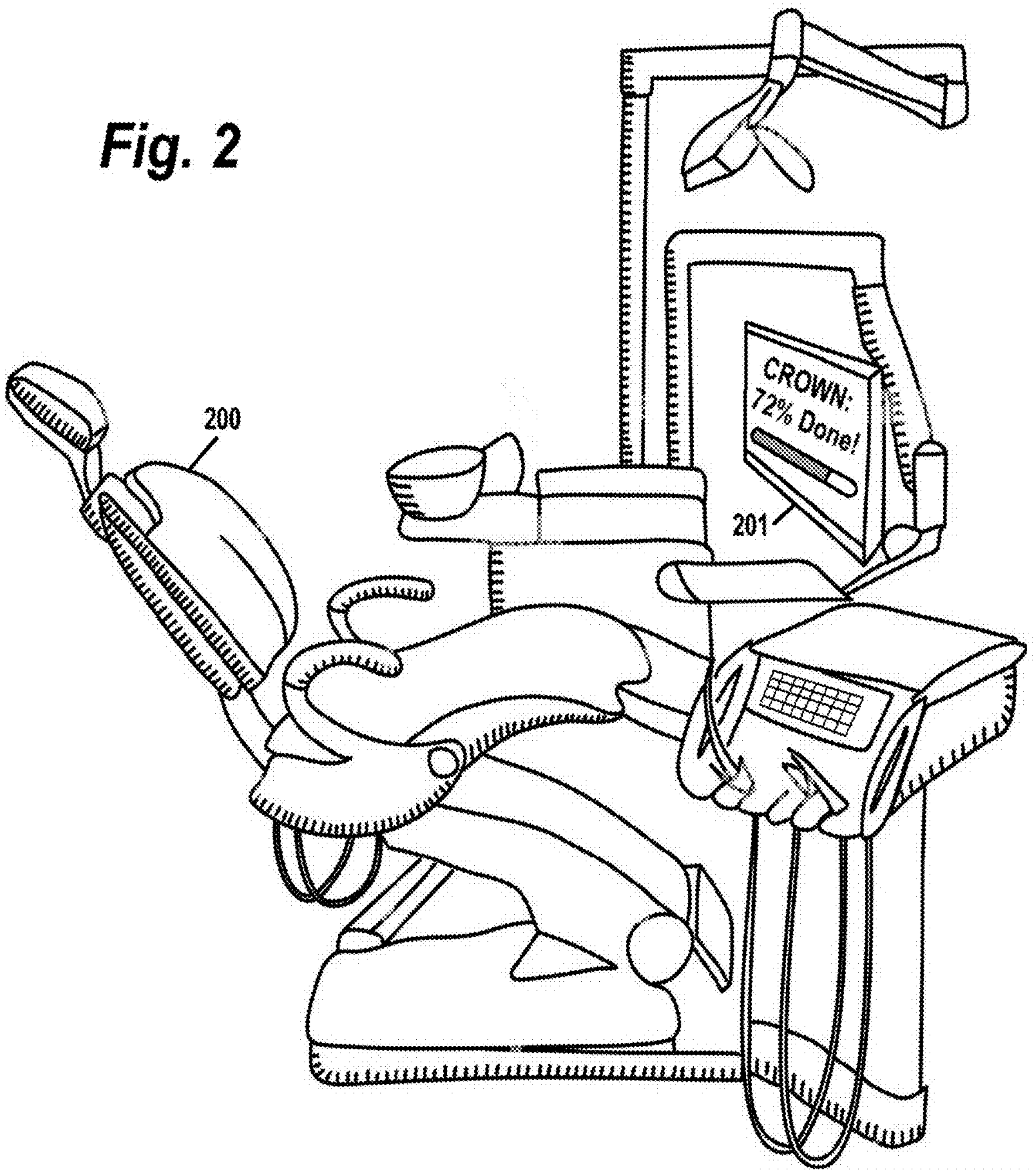
FIG. 2 is an illustration of a dental treatment chair, which displays to the dental patient on a dedicated display unit the current progress and/or the current step of the dental treatment procedure being performed, as deduced automatically and autonomously by the dental treatment system, in accordance with some demonstrative embodiments.

Reference is made to FIG. 2, which is an illustration of a dental treatment chair 200, which displays to the patient on a dedicated display unit 201 the current progress of the current dental treatment procedure, as deduced automatically and autonomously by the system, in accordance with some demonstrative embodiments. For example, the patient-facing display unit 201 displays to the patient the following demonstrative information: "CROWN", which is the name of the dental procedure; "72% Done!", which is the current percentage-based value of progress of this dental procedure; and a horizontal Progress Bar that is 72 percent filled-out and is 28 percent empty, providing a visual non-verbal indication of the progress of the dental procedure. Optionally, other progress information may be displayed, such as: (a) indication about the most-recent completed step, such as, "Just completed: X-Ray Imaging"; (b) indication about the currently-performed step, such as, "Currently doing: UV radiation of filling"; (c) indication about the next/upcoming step, such as, "Coming up/Next Step: Rinse and Spit"; (d) indication of other information or educational tips, such as, "The crown that we do today is made of Zirconia, and can last for 20 years!"; (e) indication of the time that elapsed since the patient sat on the dental treatment chair or since the dental procedure began, and/or an estimation of the time that remains to completion of the dental procedure, such as, "You are already 57 minutes into this Crown procedure, and it is estimated that we need only 25 more minutes left until completion!". These are only demonstrative and non-limiting examples; other progress-related information may be deduced and displayed to the patient, during the ongoing dental procedure; and is updated dynamically as the dental procedure progresses.

Figure 1B:
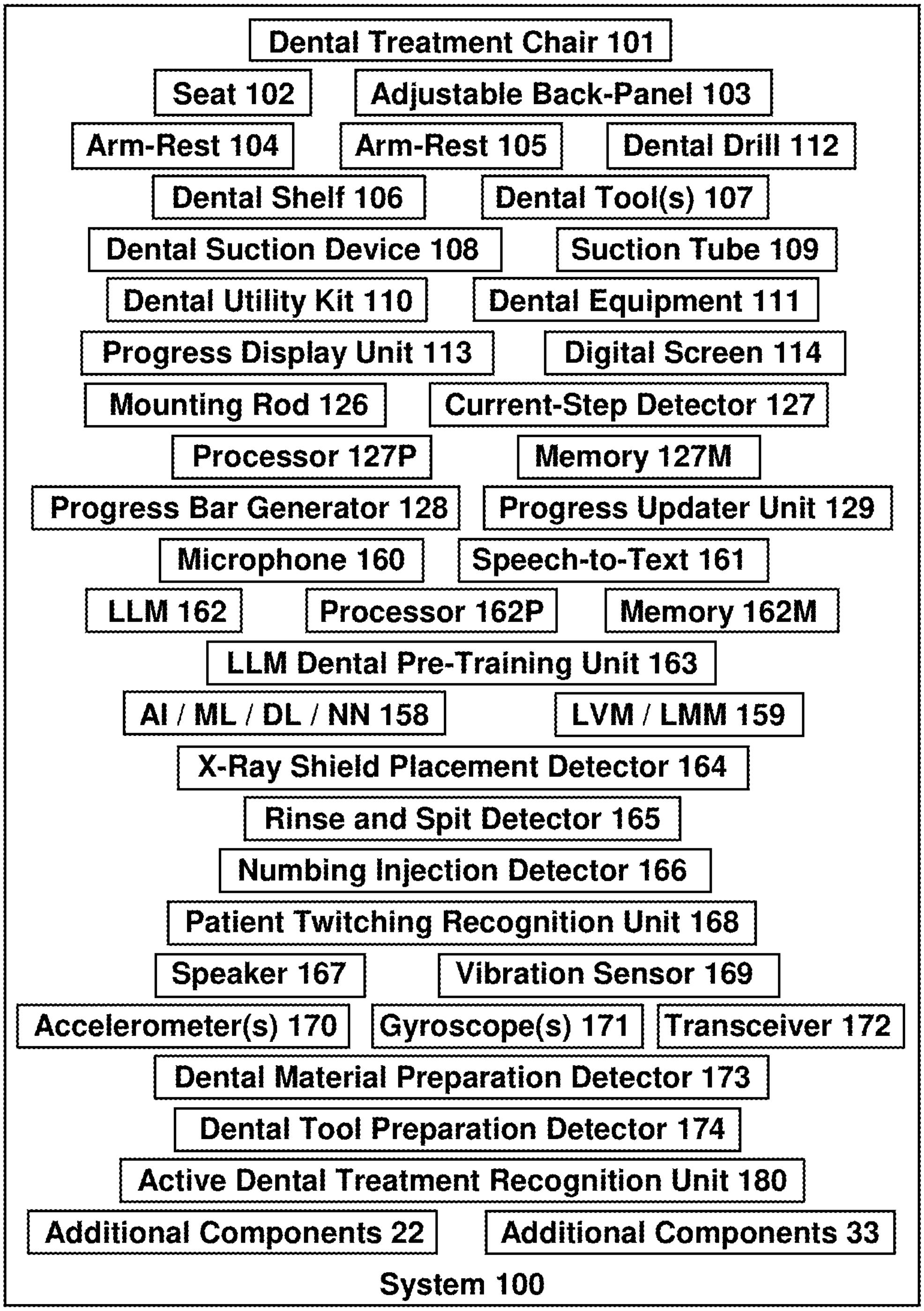
FIG. 1B is a schematic block diagram illustration of a dental treatment system, in accordance with some demonstrative embodiments.

Reference is made to FIG. 1B, which is a schematic block diagram illustration of a system 100, in accordance with some demonstrative embodiments. System 100 of FIG. 1B is a demonstrative implementation of system 50 of FIG. 1A.

Figure 1C:
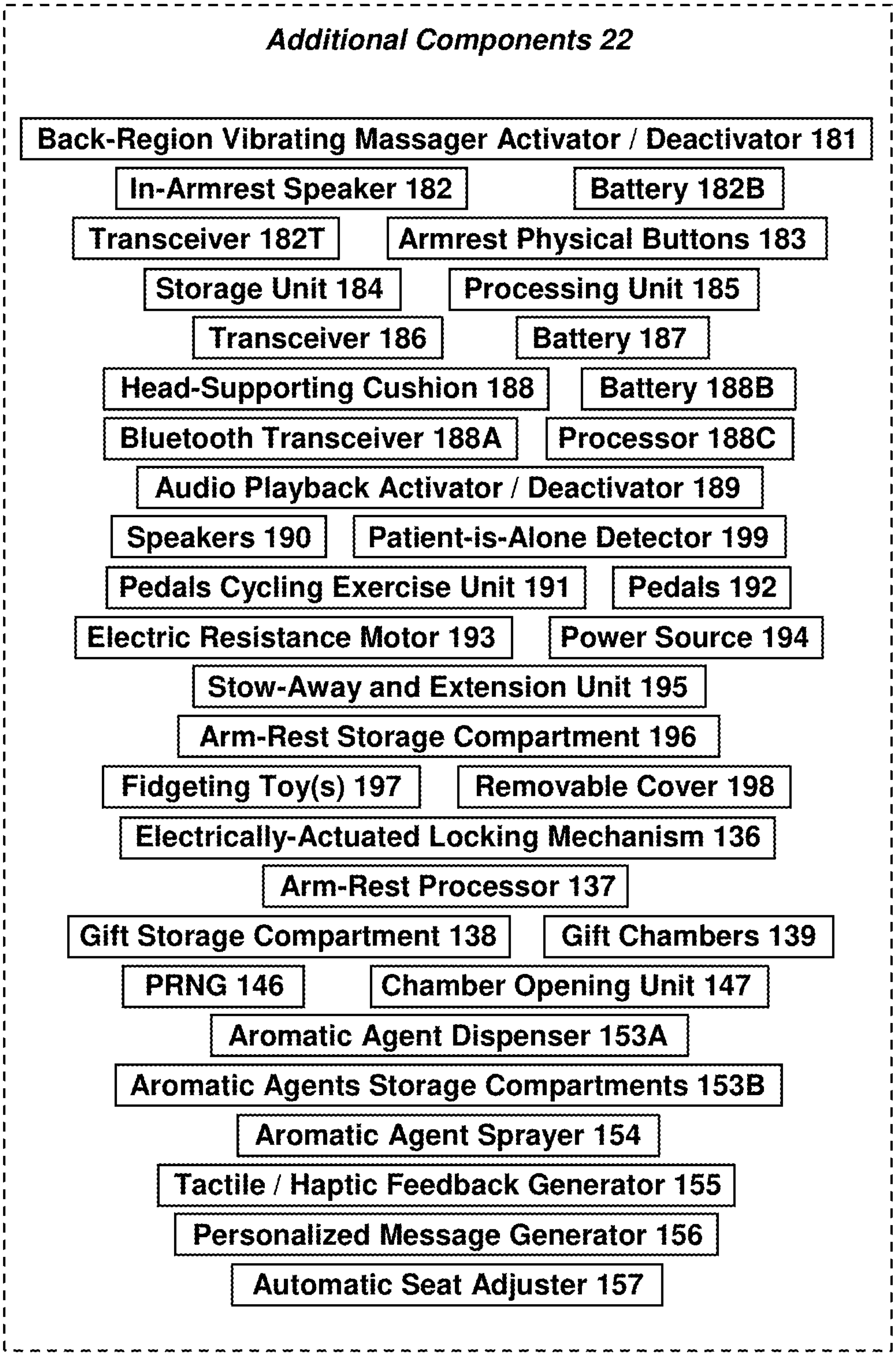
FIG. 1C is a schematic block diagram illustration of a set of additional components that are part of the dental treatment system of FIG. 1B, in accordance with some demonstrative embodiments, and that are shown as a separate drawing in order to prevent over-crowding of a drawing with numerous components.
Figure 1D:
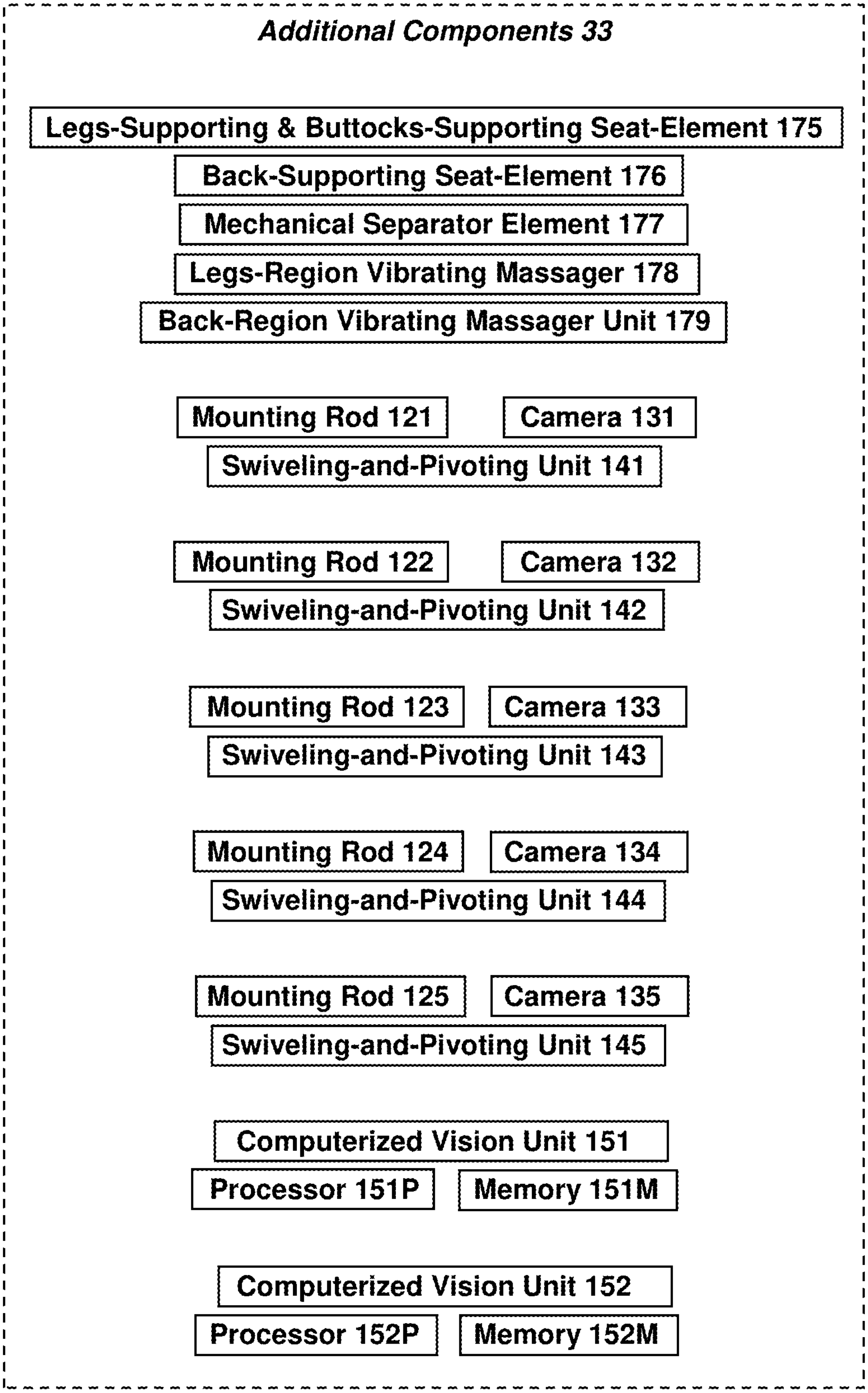
FIG. 1D is another schematic block diagram illustration of another set of additional components that are part of the dental treatment system of FIG. 1B, in accordance with some demonstrative embodiments, and that are shown as a separate drawing in order to prevent over-crowding of a drawing with numerous components.

In order to avoid over-crowding of the drawings, FIG. 1B shows "Additional Components 22" that are part of system 100 and that are then shown at a greater detail in FIG. 1C; and also, FIG. 1B shows "Additional Components 33" that are part of system 100 and that are then shown at a greater detail in FIG. 1D. Taken together, the components that are shown across FIGS. 1B and 1C and 1D, are together parts of a singular system 100, even if they are shown across multiple drawings for the sake of clarity and to avoid over-crowding of a single drawing with dozens of components.

In some embodiments, System 100 comprises a Dental Treatment Chair 101 (or a dental treatment bed), comprising: a Seat 102, an Adjustable Back-Panel 103, and two movable Arm-Rests 104-105. The dental treatment chair is configured to accommodate therein a dental treatment patient (or a dental patient), that undergoes a dental procedure (or a dental treatment), at a dentist office (or a dental clinic, or a hospital, or other dental facility or medical facility), by a dentist and optionally also by a dental assistant or dental aid. The dental treatment chair further comprises a movable shelf 106 that is adapted to carry thereon one or more dental tools 107.

The dental treatment chair comprises, or is connected to, a dental suction device 108 that is configured to suck saliva and/or fluids from a mouth of said dental treatment patient via an elongated and flexible suction tube 109. The dental treatment chair comprises, or is connected to, a dental utility kit 110 that comprises one or more dental tools or dental equipment 111, which include at least an electric dental drill 112.

In some embodiments, optionally, the dentist or dental assistant may indicate to the system in one or more ways, which particular type of dental procedure is about to begin. For example, the dentist may indicate via is computer terminal that a Dental Crown is about to begin; or the dental assistant may say out loud "Hello patient Adam, so glad to see you today for your Crown procedure in tooth number 28", and an acoustic microphone may capture that speech, a text-to-speech converter converts it into text, and the LLM or a Natural Language Processing (NLP) unit deduces or recognizes the particular dental procedure; and the system can obtain or fetch or read, from the database of dental procedures and their multiple steps, the relevant record for a typical Crown on Tooth 28, having (for example) 14 particularly steps in a 120-minute long session. This also indicates to the system to Reset to Zero a progress counter parameter, such as a parameter that is gradually increased from 0 percent to 100 percent.

The dental treatment chair further comprises: a first mounting rod 121, that is integrally connected to said dental treatment chair; a first camera 131 which is a dentist-oriented camera, that is mounted on said first mounting rod, and is configured to be oriented generally towards an upper body of said dentist, and is configured to capture real-time video of the upper body of said dentist; and a first swiveling-and-pivoting unit 141, that is configured to mechanically swivel and pivot the first camera based on swiveling and pivoting signals;

The dental treatment chair further comprises: a second mounting rod 122, that is integrally connected to said dental treatment chair; a second camera 132 which is a dental assistant oriented camera, that is mounted on said second mounting rod, and is configured to be oriented generally towards an upper body of said dental assistant, and is configured to capture real-time video of the upper body of said dental assistant; and a second swiveling-and-pivoting unit 142, that is configured to mechanically swivel and pivot the second camera based on swiveling and pivoting signals.

The dental treatment chair further comprises: a third mounting rod 123, that is integrally connected to said dental treatment chair; a third camera 133 which is a patient-face oriented camera, that is mounted on said third mounting rod, and is configured to be oriented generally towards a face of said dental treatment patient, and is configured to capture real-time video of the face of said dental treatment patient; and a third swiveling-and-pivoting unit 143, that is configured to mechanically swivel and pivot the third camera based on swiveling and pivoting signals.

The dental treatment chair further comprises: a fourth mounting rod 124, that is integrally connected to said dental treatment chair; a fourth camera 134 which is patient-body oriented camera, that is mounted on said fourth mounting rod, and is configured to be oriented generally towards a torso and legs of said dental treatment patient, and is configured to capture real-time video of the torso and legs of said dental treatment patient; and a fourth swiveling-and-pivoting unit 144, that is configured to mechanically swivel and pivot the fourth camera based on swiveling and pivoting signals.

The dental treatment chair further comprises: a fifth mounting rod 125, that is integrally connected to said dental treatment chair; a fifth camera 135 which is an office-oriented camera, that is mounted on said fifth mounting rod, and is configured to be oriented generally towards a field-of-view that comprises a majority of said dentist office that includes said dental treatment chair and said dentist and said dental assistant; wherein the fifth camera is configured to capture real-time video of said majority of said dentist office. Optionally, a fifth swiveling-and-pivoting unit 145 is operational, and is configured to mechanically swivel and pivot the fifth camera based on swiveling and pivoting signals; although in some implementations the fifth camera may be fixedly mounted and need not necessarily be capable of pivoting or swiveling.

The dental treatment chair further comprises: a first Computerized Vision unit 151, that is implemented using at least a first hardware processor 151P and a first memory unit 151M; wherein the first Computerized Vision unit is configured: (g1) to receive real-time video from the first camera; (g2) to receive real-time video from the second camera; (g3) to receive real-time video from the third camera; (g4) to receive real-time video from the fourth camera; (g5) to receive real-time video from the fourth camera; (g6) to perform computerized vision analysis of the real-time video from the first camera and the real-time video from the second camera and the real-time video from the third camera and the real-time video from the fourth camera and the real-time video from the fifth camera; (g7) based on said computerized video analysis, to generate Swivel-and-Pivot Commands that are transferred to the first swiveling-and-pivoting unit and that cause the first swiveling-and-pivoting unit to dynamically swivel and pivot the first camera to be oriented towards said dentist; (g8) based on said computerized video analysis, to generate swivel-and-pivot commands that are transferred to the second swiveling-and-pivoting unit and that cause the second swiveling-and-pivoting unit to dynamically swivel and pivot the second camera to be oriented towards said dental assistant; (g9) based on said computerized video analysis, to generate swivel-and-pivot commands that are transferred to the third swiveling-and-pivoting unit and that cause the third swiveling-and-pivoting unit to dynamically swivel and pivot the third camera to be oriented towards the face of said dental treatment patient;

(g10) based on said computerized video analysis, to generate swivel-and-pivot commands that are transferred to the fourth swiveling-and-pivoting unit and that cause the fourth swiveling-and-pivoting unit to dynamically swivel and pivot the fourth camera to be oriented towards the torso and legs of said dental treatment patient.

The dental treatment chair further comprises: a second Computerized Vision unit 152, that is implemented using at least a second hardware processor 152P and a second memory unit 152M; wherein the second Computerized Vision unit is configured: (H1) to receive real-time video from the first camera; (H2) to receive real-time video from the second camera; (H3) to receive real-time video from the third camera; (H4) to receive real-time video from the fourth camera; (H5) to receive real-time video from the fourth camera; (H6) to perform computerized vision analysis of the real-time video from the first camera and the real-time video from the second camera and the real-time video from the third camera and the real-time video from the fourth camera and the real-time video from the fifth camera; (H7) based on said computerized vision analysis of (H6), to recognize that a particular step in said dental procedure is occurring, and to generate a Current Step Estimation Signal indicating which step in said dental procedure is estimated to be currently occurring based on computerized vision analysis.

The dental treatment chair further comprises: a Progress Display Unit 113, comprising a Digital Screen 114 (e.g., monitor, LED screen, OLED screen) that is that is integrally connected to said dental treatment chair via a sixth mounting rod 126; wherein said Progress Display Unit is oriented to be in a field-of-view of a said dental treatment patient.

The dental treatment chair further comprises: a Current-Step Detector Unit 127, implemented by utilizing at least a third hardware processor 127P and a third memory unit 127M. The Current-Step Detector Unit is configured: (J1) to determine a current step of the dental procedure, based at least on: (i) the Current Step Estimation Signal that was generated by the second Computerized Vision unit based on computerized vision analysis of real-time video from the first camera and the second camera and the third camera and the fourth camera and the fifth camera, and also, (ii) a multiple-step dental treatment plan that is pre-defined for said dental procedure and that indicates a series of planned consecutive steps of said dental procedure; and (J2) to determine a current Progress Percentage Value, in a range of 0 to 100 percent, indicating an estimated percentage of said dental procedure that has been completed.

The dental treatment chair further comprises: a Progress Bar Generator Unit 128, configured to generate a graphical representation of a progress bar corresponding to said current Progress Percentage Value; optionally by using its own hardware processor and memory unit.

The dental treatment chair further comprises: (J4) a Progress Updater Unit 129, configured to command the Progress Display Unit to dynamically display thereon an output that conveys at least: (a) the current Progress Percentage Value, in said range of 0 to 100 percent, and also (b) the graphical representation of the progress bar corresponding to said current Progress Percentage Value, and also (c) a textual title indicating the current step that is occurring in the dental procedure. These may be performed by using a pre-defined database or dataset that correlates or matches between a recognize dental event or action (e.g., assistant gives to dentist a filling material; or, dentist is activating the dental drill) and a corresponding step or progress-level in a dental procedure.

In some embodiments, optionally, a Database of Dental Steps and Procedures 130 may be used, storing pre-defined data that enables the above-mentioned operations and/or the operations discussed below. For example, for the dental procedure of "replacing an old filling with a new filling", the database may store and indicate the following information: (a) Patient sits on the dental chair, cumulative progress is now 2 percent; (b) Patient is now covered by the X-Ray protective blanket, cumulative progress is now 5 percent; (c) Dental Assistant is now aiming the X-Ray tube camera towards the patient's mouth, cumulative progress is now 7 percent; (d) Dental Assistant existed the room to push the X-Ray button and returned to the room, cumulative progress is now 9 percent; (e) Dentist entered the room and reviews the X-Ray image, cumulative progress is now 12 percent; (f) Saliva Suction Tube activated and inserted into patient's mouth, cumulative progress is now 20 percent; (g) Dentist starts using the dental drill to clean out the old filling, cumulative progress is now 28 percent; (h) Dentist stopped using the dental drill, cumulative progress is now 42 percent; (i) Assistant is mixing the filling material, cumulative progress is now 50 percent; (j) Dentist is inserting filling material into patient's mouth, cumulative progress is now 65 percent; (j) Assistant is shining ultra-violet light onto the filling to expedite its curing, cumulative progress is now 75 percent; (k) Dentist is using the dental drill again to smoothen the surface of the new filling, cumulative progress is now 87 percent; (1) Assistant gives to patient a liquid to rinse and spit, cumulative progress is now 95 percent; (m) Assistant gives to patient a "loot bag" or "goodies bag" with a gift toothbrush, cumulative progress is now 100 percent and the dental procedure is completed. This is only a non-limiting example.

In some embodiments, the dental treatment chair further comprises: (K1) an acoustic microphone 160, configured to capture audio from a vicinity of the dental treatment chair; (K2) a speech-to-text converter unit 161, configured to convert captured audio from said acoustic microphone into a textual transcript of speech uttered in the vicinity of the dental treatment chair; (K3) a Large Language Model (LLM) Unit 162, implemented by utilizing at least a fourth hardware processor 162P and a fourth memory unit 162M; implemented as a locally-running/co-located unit, or as a remote or cloud-based unit that is accessible via an Internet connection using a transceiver. The LLM Unit is configured to receive as inputs: (i) said textual transcript of speech uttered in the vicinity of the dental treatment chair, and also (ii) a textual description of said multiple-step dental treatment plan, and also (iii) a pre-defined title of the dental procedure that is being performed. The LLM Unit is configured, via a pre-defined LLM prompt, to automatically generate a textual output that indicates which particular step of the dental treatment plan is currently being performed. The textual output that is generated by the LLM Unit, that indicates which particular step of the dental treatment plan is currently being performed, is utilized as additional input by the Current-Step Detector Unit for determining the current step that is currently occurring in the dental procedure.

In some embodiments, instead of using the LLM unit, or in addition to it, one or more other units may be used; for example, an Artificial Intelligence (AI) unit, a Machine Learning (ML) unit, a Deep Learning (DL) unit, a Neural Network (NN) or Deep Neural Network (DNN) or Convolutional Neural Network (CNN) or Deep CNN; or a Vision and Language Model (VLM) or a Language and Vision Model (LVM) or a similar Large Multimodal Model (LMM)

or a large multiple-modalities model that can process data from two or more modalities (e.g., visual, textual, images, video frames, videos, audio, spreadsheets, tabular data). For demonstrative purposes, such optional/additional units are shown as ML/DL/NN 158, and as LVM/LMM 159; and they may be configured to detect or deduce the current step or stage of a dental treatment procedure, based on the data available to them.

In some embodiments, wherein the LLM Unit is specifically trained and/or pre-trained via a LLM Dental Pre-Training Unit 163 on a body-of-knowledge that comprises: (i) a first list of textual titles of dental procedures, and (ii) a second list of detailed textual descriptions that textually explain each step and all steps of each dental procedure.

In some embodiments, the system further comprises: an X-Ray Shield Placement Detector 164, that is configured to perform computerized vision analysis of real-time video captured by the first camera, the second camera, the third camera, the fourth camera, and the fifth camera; and to determine from said computerized vision analysis that an X-Ray protective blanket was placed onto the dental treatment patient; and to generate an X-Ray Shield Placement Signal that indicates that computerized vision analysis of real-time video has recognized that said the X-Ray protective blanket was placed onto the dental treatment patient. The Current-Step Detector Unit is configured to increase, by at least 1 percent-point of progress, a current value of the current Progress Percentage Value in response to said X-Ray Shield Placement Signal.

It is noted that the value of current progress of the dental treatment, may be reset to zero upon commencement of a new dental treatment; and may be monitored by the system to never pass 100 percent. For example, if a particular pre-defined rule or condition indicates that the progress percentage value should be increased by N percentage-points if a particular event is sensed, and such increase would cause the progress score to surpass 100 (or 99, or 95) percent points, then the system increases the progress score by only 0.001 percent points, or by zero percent points, to ensure that the progress score does not pass 100, or does not pass another pre-defined limit (such as 99 or 95 percent, reserving the last few percentage points to the detection of a final stage of a multi-stage dental procedure)

In some embodiments, the system further comprises: a Rinse and Spit Detector 165, that is configured to perform computerized vision analysis of real-time video captured by the first camera, the second camera, the third camera, the fourth camera, and the fifth camera; and to determine from computerized vision analysis that the dental patient performed a rinse and spit procedure; and to generate a Rinse and Spit Recognition Signal that indicates that computerized vision analysis of real-time video has recognized that said Rinse and Spit Recognition Signal was performed. The Current-Step Detector Unit is configured to increase, by at least 1 percent-point of progress, a current value of the current Progress Percentage Value in response to said Rinse and Spit Recognition Signal.

In some embodiments, the system further comprises: a Numbing Injection Detector 166, that is configured to perform computerized vision analysis of real-time video captured by the first camera, the second camera, the third camera, the fourth camera, and the fifth camera; and to determine from computerized vision analysis that the dental patient is currently receiving a numbing injection; and to generate a Numbing Injection Recognition Signal that indicates that computerized vision analysis of real-time video has recognized that said numbing injection was performed. The Current-Step Detector Unit is configured to increase, by at least 1 percent-point of progress, a current value of the current Progress Percentage Value in response to said Numbing Injection Recognition Signal.

In some embodiments, the dental treatment chair further comprises: (N1) an acoustic speaker 167, configured to playback pre-recorded audio messages; (N2) a Patient Twitching Recognition Unit 168, comprising: a Vibration Sensor 169 integrated in the dental treatment chair, one or more Accelerometers 170 integrated in the dental treatment chair, and one or more gyroscopes units 171 integrated in the dental treatment chair. Based on sudden changes in values that are sensed by said Vibration Sensor and by said one or more accelerometers and by said one or more gyroscopes units, the Patient Twitching Recognition Unit is configured to estimate that at least one body part of said dental patient is twitching, and to generate a Patient Twitching Recognition signal. The Patient Twitching Recognition Unit is further configured to trigger said acoustic speaker, to playback a particular pre-recorded audio message indicating that the dental patient is twitching, based on said Patient Twitching Recognition signal. This message may be helpful for the Dentist to become aware of this information. In some embodiments, the audio message is coded or encoded, such that instead of playing an audio message that says "The patient is twitching", an encoded audio message is played, saying "Today is a beautiful day and we had made great progress", which helps to make the patient relaxed, and also indicates or hints to the Dentist that the patient is actually twitching or in pain.

In some embodiments, the Patient Twitching Recognition Unit is configured to estimate whether or not said dental patient is twitching, based cumulatively on: (i) data sensed by the Vibration Sensor integrated in the dental treatment chair, data sensed by the one or more accelerometers integrated in the dental treatment chair, and data sensed by the one or more gyroscopes units integrated in the dental treatment chair; and also, (ii) results of a Computerized Vision analysis process, that performs computerized vision analysis of real-time video captured by the first camera, the second camera, the third camera, the fourth camera, and the fifth camera, wherein said Computerized Vision analysis process is specifically configured to recognize visual indications of patient twitching events.

In some embodiments, the dental treatment chair further comprises: a Wireless Transceiver 172, such as a Wi-Fi or Bluetooth™ transceiver, configured to wirelessly communicate with a point-of-sale terminal of said dentist office. In some embodiments, if more than N Patient Twitching Recognition signals are generated within a dental procedure of said dental patient by the Patient Twitching Recognition Unit, or within T minutes, then the wireless transceiver of the dental treatment chair wirelessly transmits a Discount Generation Message to said point-of-said terminal, indicating that said dental patient is entitled to a particular price discount for said dental treatment procedure due to automatic recognition of excessive twitching.

In some embodiments, the system further comprises: a Dental Material Preparation Detector 173 (or recognition unit), that is configured to perform computerized vision analysis of real-time video captured by the first camera, the second camera, the third camera, the fourth camera, and the fifth camera, and to determine from computerized vision analysis that a dental material (e.g., dental filling material) is being prepared towards insertion into a mouth of the dental patient, by recognizing that a dental filling material is mixed or is extracted from a container and becomes readily available for insertion; and to generate a Dental Material Preparation Recognition Signal that indicates that computerized vision analysis of real-time video has recognized that preparation of said dental material was performed. The Current-Step Detector Unit is configured to increase, by at least 1 percent-point of progress, a current value of the current Progress Percentage Value in response to said Dental Material Preparation Recognition Signal.

In some embodiments, the system comprises: a Dental Tool Preparation Detector 174, that is configured to perform computerized vision analysis of real-time video captured by the first camera, the second camera, the third camera, the fourth camera, and the fifth camera; and to determine from computerized vision analysis that a particular dental tool is being prepared towards utilization on said dental patient, by recognizing that said particular dental tool is being placed in proximity to said dental patient and becomes readily available for utilization by said dentist; and to generate a Dental Tool Preparation Recognition Signal that indicates that computerized vision analysis of real-time video has recognized that preparation of said dental tool was performed. The Current-Step Detector Unit is configured to increase, by at least 1 percent-point of progress, a current value of the current Progress Percentage Value in response to said Dental Tool Preparation Recognition Signal.

In some embodiments, the seat of the dental treatment chair comprises: (R1) a Legs-Supporting and Buttocks-Supporting Seat-Element 175, configured to support legs and buttocks of the dental patient; (R2) a Back-Supporting Seat-Element 176, configured to support a back of the dental patient; (R3) a Mechanical Separator Element 177, having an upper edge and a lower edge; wherein the upper edge of the mechanical separator element is connected to the back-supporting seat-element; wherein the lower edge of the mechanical separator element is connected to the legs-supporting and buttocks-supporting seat-element. The mechanical separator element is configured to spatially and operationally separate between (i) the back-supporting seat-element and (ii) the legs-supporting and buttocks-supporting seat-element. An additional component is (R4) a Legs-Region Vibrating Massager Unit 178, located within the legs-supporting and buttocks-supporting seat-element of the seat of the dental treatment chair. The legs-region vibrating massager unit, that is located within the legs-supporting and buttocks-supporting seat-element of the seat of the dental treatment chair, is configured to vibrate and to provide a massage to the legs of the dental treatment patient. The legs-region vibrating massager unit is configured to continuously vibrate, even when the dental treatment patient is being touched and actively treated by said dentist or said assistant. The legs-supporting and buttocks-supporting seat-element is vibrating when the legs-region vibrating massager unit is operational. The mechanical separator element absorbs some or all vibrations and/or prevents vibrations, that are generated at the legs-region vibrating massager, from propagating into the back-supporting seat-element. The back-supporting seat-element remains generally idle and non-vibrating, while the legs-region vibrating massager is operational.

In some embodiments, the back-supporting seat-element of the seat of the dental treatment chair comprises a Back-Region Vibrating Massager Unit 179; which operates non-continuously, and selectively operates only at time-periods in which computerized vision analysis of real-time video captured by the first camera, the second camera, the third camera, the fourth camera, and the fifth camera, indicates that the dental treatment patient is not being touched by the dentist or the assistant. For example, the system comprises an Active Dental Treatment Recognition Unit 180, that is configured to perform computerized vision analysis of real-time video captured by the first camera, the second camera, the third camera, the fourth camera, and the fifth camera; and to determine from computerized vision analysis that the dentist or the assistant or both are currently touching a face or a body of the dental treatment patient, directly or via a dental treatment tool; and to generate an Active Dental Treatment Recognition Signal that indicates that computerized vision analysis of real-time video has recognized that the dentist or the assistant or both are currently touching the face or the body of the dental treatment patient.

In some embodiments, the system comprises a Back-Region Vibrating Massager Activator/Deactivator Unit 181, that is configured: (i) to deactivate the back-region vibrating massager as long as the Active Dental Treatment Recognition Signal is generated by the Active Dental Treatment Recognition Unit, and (ii) to activate the back-region vibrating massager when the Active Dental Treatment Recognition Signal is no longer generated by the Active Dental Treatment Recognition Unit.

In some embodiments, the two moveable arm-rests (104, 105) of the dental treatment seat comprise a first arm-rest and a second arm-rest. The first arm-rest of the dental treatment chair comprises: an In-Armrest Speaker 182, that is embedded within the first arm-rest, and that is connected to a first battery 182B and to a first wireless/Bluetooth™ transceiver 182T; wherein the acoustic speaker 182 is configured to play audio based on incoming audio data that is wirelessly received by the first Bluetooth™ transceiver of the first arm-rest. In some embodiments, the second arm-rest of the dental treatment chair comprises: (a) a set of Armrest Physical Buttons 183 that enable the dental treatment patient to input audio playback commands; wherein the audio playback commands include at least: a command to increase playback volume, a command to decrease playback volume, a command to skip to a next audio clip, a command to pause playback, a command to resume playback; (b) a Storage Unit 184, configured to store therein a plurality of audio files, each audio file corresponding to a different song (or audio lecture, or podcast, or other audio content); (c) a processing unit 185, configured to process a user-selected audio file that is stored in said storage unit, and to generate signals that enables the acoustic speaker to playback said user-selected audio file; (d) a second wireless/Bluetooth™ transceiver 186, that is embedded within the second arm-rest, and that is connected to a second battery 187.

The second Bluetooth™ transceiver that is embedded within the second arm-rest, wirelessly transmits over a wireless communication link, to the first Bluetooth™ transceiver that is embedded within the first arm-rest, data and signals that cause the acoustic speaker that is embedded within the first arm-rest to play songs and to modify playback of songs based on user-commands that are inputted via the set of physical buttons of the second arm-rest.

In some embodiments, the dental treatment seat further comprises: a Head-Supporting Cushion 188, which integrally embeds therein: (i) a Bluetooth™ transceiver 188A, and (ii) a battery 188B, and (iii) an internal hardware processor 188C, and (iv) an Audio Playback Activator/Deactivator Unit 189, and (v) a pair of stereo speakers 190; and (vi) a Patient-is-Alone Detector Unit. The Bluetooth™ transceiver of the Head-Supporting Cushion of the dental treatment chair is configured to receive, from the second Bluetooth™ transceiver that is embedded within the second arm-rest of the dental treatment chair, data and signals that cause the pair of stereo speakers that are embedded within the Head-Supporting Cushion to play songs and to modify playback of songs based on user-commands that are inputted via the set of physical buttons of the second arm-rest. The Patient-is-Alone Detector Unit, that is embedded within the Head-Supporting Cushion of the dental treatment chair, is configured to perform computerized vision analysis of real-time video captured by the first camera, the second camera, the third camera, the fourth camera, and the fifth camera; and to determine from computerized vision analysis that both the dentist and the assistant are not within field-of-view of any of the first camera, the second camera, the third camera, the fourth camera, and the fifth camera; and to generate a Patient-is-Alone Signal, and to continue to generate said Patient-is-Alone Signal at one second intervals as long as said computerized vision analysis continues to indicate that both the dentist and the assistant are not within field-of-view of any of the first camera, the second camera, the third camera, the fourth camera, and the fifth camera. The Audio Playback Activator/Deactivator Unit, that is embedded in the Head-Supporting Cushion, is configured: (i) to automatically activate audio playback via the pair of stereo speakers, in response to receiving said Patient-is-Alone Signal; and (ii) to automatically deactivate audio playback via the pair of stereo speakers, once the Patient-is-Alone Signal is no longer received from the Patient-is-Alone Detector Unit.

In some embodiments, the dental treatment seat further comprises: (T1) a Pedals Cycling Exercise Unit 191, that is located at or near a lower edge of the dental treatment chair; comprising two Pedals 192 that accommodate two feet of the dental treatment patient, that are capable of spinning in response to spinning operations by the two feet of the dental treatment patient; and further comprising an Electric Resistance Motor 193 (or, an Electric Resistance-Generating Motor) that electrically generates mechanical resistance that resists said spinning of the two Pedals in accordance with a particular Resistance Level is that user-selected via a mechanical Knob that is connected to said Electric Resistance Motor; and a power source 194 (e.g., battery, or cable or wire that connects to a mains electricity power outlet) that provides electric power to said Electric Resistance Motor; (T2) a Stow-Away and Extension Unit 195, that is configured to switch the Pedals Cycling Exercise Unit from a Stowed-Away position to an Extended position, and from said Extended position to said Stowe-Away position. In said Stowed-Away position, the Pedals Cycling Exercise Unit is stowed away beneath the dental treatment chair, and is not accessible to the feet of the dental treatment patient. In said Extended position, the Pedals Cycling Exercise Unit is accessible by the two feet of the dental treatment patient. The Stow-Away and Extension Unit is configured to trigger switching of the Pedals Cycling Exercise Unit to said Extended Position, in response to a detection that the Patient-is-Alone signal is generated for at least five consecutive seconds, wherein N is a pre-defined positive number. The Stow-Away and Extension Unit is configured to trigger switching of the Pedals Cycling Exercise Unit to said Stowed-Away Position, in response to a detection that the Patient-is-Alone signal was not generated for at least two seconds.

In some embodiments, the dental treatment seat further comprises: an Arm-Rest Storage Compartment 196, that is integrally built into the first arm-rest of the dental treatment seat; and one or more Fidgeting Toy(s) 197 (e.g., a fidgeting cube, an elastic ball that can be squeezed, a pressure ball) that are stored within the Arm-Rest Storage Compartment. Each of said one or more fidgeting toys is structured to enable manual fidgeting of the dental treatment patient or to enable light physical therapy or therapeutic activity or anxiety-reducing activity; a Removable Cover 198, that removably covers said Arm-Rest Storage Compartment, and that conceals content stored within the Arm-Rest Storage Compartment; an Electrically-Actuated Locking Mechanism 136, that locks said Removable Cover to said Arm-Rest Storage Compartment and that blocks the removal or the opening of said Removable Cover unless a Cover-Opening Signal is received at said electrically-actuated locking mechanism and triggers said electrically-actuated locking mechanism to unlock the Removable Cover; an Arm-Rest Hardware Processor 137, that is embedded within the first arm-rest of the dental treatment seat, and is associated with a co-located battery and memory unit that stores code. The arm-rest hardware processor is configured to continuously monitor whether or not a Patient-is-Alone Signal is generated by the Patient-is-Alone Detector Unit. The arm-rest hardware processor is configured to generate a signal that commands the electrically-actuated locking mechanism to unlock the Removable Cover of the Arm-Rest Storage Compartment, and to enable access of the dental treatment patient to the one or more fidgeting toys that are stored within the Arm-Rest Storage Compartment, upon detection that Patient-is-Alone Signals were generated by the Patient-is-Alone Detector Unit for at least 5 consecutive seconds.

In some embodiments, the dental treatment seat further comprises: a Gift Storage Compartment 138, that is integrally connected to the second arm-rest of the dental treatment seat. The Gift Storage Compartment is divided into three Gift Chambers 139 that are a first chamber, a second chamber, and a third chamber. The first chamber of the Gift Storage Compartment stores therein a gift toothbrush, and has a first Chamber Cover that covers the first chamber. The second chamber of the Gift Storage Compartment stores therein a gift toothpaste tube, and has a second Chamber Cover that covers the second chamber. The third chamber of the Gift Storage Compartment stores therein a gift dental floss, and has a third Chamber Cover that covers the third chamber. Further included in the dental treatment chair is a Pseudo-Random Number Generator 146 (or PRNG 146), that pseudo-randomly selects a single number from the group consisting of: one, two, three; a Chamber Opening Unit 147, that is configured to selectively open only one of the first Chamber Cover, the second Chamber Cover, and the third Chamber Cover, in response to the single number that was pseudo-randomly selected by the Pseudo-Random Number Generator. The dental treatment seat thus provides to each dental treatment patient a single gift, selected pseudo-randomly from said three chambers.

In some embodiments, the dental treatment seat further comprises: an Aromatic Agent Dispenser Unit 153A, configured to selectively dispense a spraying dose of a particular aromatic agent, from a plurality of discrete Aromatic Agents Storage Compartments 153B, via an Aromatic Agent Sprayer Unit 154; wherein completion of each particular step in a multi-step dental procedure, automatically triggers a spraying of a particular pre-defined aromatic agent. For example, detection of the completion of the step "taking an X-Ray image", may be pre-defined to automatically trigger the spraying of a Vanilla scent; whereas, completion of the step "the filling material was inserted into the tooth cavity", may be pre-defined to automatically trigger the spraying of a Cherry scent.

In some embodiments, the dental treatment seat further comprises: a Tactile/Haptic Feedback Generator 155, that is embedded within the dental treatment chair, and that is configured to generate a particular pre-defined pattern of tactile feedback to said dental patient, upon detection that a particular step in a multi-step dental procedure is completed. For example, detection of the completion of the step "taking an X-Ray image", may be pre-defined to automatically trigger the generation of tactile feedback of three tactile/haptic pulses with time-gaps of one second in between them; whereas, completion of the step "the filling material was inserted into the tooth cavity", may be pre-defined to automatically trigger the generation of tactile feedback of five tactile/haptic pulses with time-gaps of two seconds in between them.

In some embodiments, the dental treatment seat further comprises: a Personalized Message Generator 156, that selects and displays a particular encouragement message to said dental patient, upon detection that a particular step in a multi-step dental procedure is completed, and based on the particular step that is completed. For example, detection of the completion of the step "taking an X-Ray image", may be pre-defined to automatically trigger the generation and the display of the message "good news, the X-Ray stage is over"; whereas, completion of the step "the filling material was inserted into the tooth cavity", may be pre-defined to automatically trigger the generation and the display of the message "fantastic news, we are almost done with the filling step".

In some embodiments, the dental treatment chair may comprise an Automatic Seat Adjuster 157, configured to automatically modify a reclining angle of the dental treatment chair, upon detection that a particular step in a multi-step dental procedure is completed, and in preparation for a next step is said multi-step dental procedure. For example, detection of the completion of the step "taking an X-Ray image", may be pre-defined to automatically modify the angular orientation of the dental chair to recline downwardly and to assume a laying-down position; whereas, completion of the step "the filling material was inserted into the tooth cavity", may be pre-defined to automatically modify the angular orientation of the dental chair to fold back upwardly and to assume a seating position.

In accordance with some embodiments, the Current Step of the dental procedure and/or the Progress of the dental procedures are not measured or computed based on Elapsed Time, and are Not a function or time; as such measurement or estimate, realized the Applicant, may not be sufficiently accurate for many situations. For example, in some implementations, the dentist may announce verbally and vocally that "we now start a two-hour procedure to do a dental crown on tooth number 27", and a database may indicate that a dental crown typically requires 120 minutes on the dentist chair; however, the Applicant has realized that such time-based progress estimate is often incorrect, as some dental procedures are performed much faster than expected, or much slower than expected (e.g., due to complications, or due to the dentist being called to handle another patient in parallel in another treatment room), or sometimes the dental patient sits on the dental chair for 20 minutes just waiting for the dentist to come or to continue the treatment; and therefore, the Applicant has provided the systems and methods of the present invention, that do not rely on the passage of time as a measurement of progress of the dental treatment, but rather, use computerized video analysis of real time video feeds from multiple cameras, and further use LLM based analysis of textual utterances and speech that are uttered by the dentist and/or the dental assistant, and/or other indicator that are time-independent as described above and/or further herein.

Some embodiments may provide a smart dental treatment chair system, comprising: a plurality of cameras configured to capture real-time video from multiple perspectives; a computerized vision system configured to analyze said video and determine the current stage of dental treatment; and a display unit configured to visually provide progress updates to a dental patient based on the analysis.

Some embodiments may provide an intelligent dental chair apparatus, equipped with multiple mounted cameras for real-time video capture and computerized vision analysis components that autonomously detect different stages of dental procedures, the apparatus further including a progress display mechanism to indicate treatment progression to the patient.

Some embodiments may provide a method for monitoring dental treatment progress, including: capturing video through several strategically placed cameras around a dental treatment chair, analyzing the captured video using a computer vision system to ascertain the treatment phase, and displaying the treatment progress on a screen visible to the patient.

Some embodiments may provide a dental procedure communication system, integrated into a dental treatment chair, comprising multiple video cameras for capturing actions and events during dental procedures, a processing unit for analyzing said videos to determine the procedure's progress, and a digital display to show a dynamic progress bar and textual information about the procedure steps directly to the patient.

Some embodiments may provide an advanced dental treatment chair, including a network of cameras providing video feeds, a processing system to analyze these feeds to identify dental treatment stages, and an interactive display system to present a progress bar and step-by-step treatment information to the dental patient.

Some embodiments may provide a dental chair configured to enhance patient engagement, comprising video acquisition devices positioned to monitor the treatment area, a computational analysis module to process video data and identify specific treatment stages, and an output device to provide real-time treatment progress to the patient using visual indicators such as progress bars or icons.

Some embodiments may provide a system for providing dental procedure updates to patients, the system featuring a dental chair with integrated video cameras, a real-time analysis unit to interpret video data to determine the current dental procedure phase, and a patient-facing display system that updates dynamically based on the analysis.

Some embodiments may provide a dental treatment observation chair, designed with an array of cameras for capturing ongoing treatment, a central processing unit for deciphering stages from the captured footage, and a patient-oriented interface that graphically displays the treatment's current phase and overall progress.

Some embodiments may provide a patient-informative dental chair system, utilizing multiple orientation-specific cameras to record procedural events, a dedicated vision analysis system to process these recordings to pinpoint treatment milestones, and an integrated display system to provide visual feedback on treatment progression to the patient.

Some embodiments may provide an autonomous dental progress monitoring chair, featuring a set of strategically placed or mounted video cameras around the chair, a computer vision unit to analyze the videos for recognition of treatment stages, and a patient-centric display that offers a visual representation of the treatment progress and upcoming steps.

In some embodiments, at least one of the mounted cameras is oriented towards the dentist to capture facial and upper body movements. In some embodiments, at least one of the mounted cameras is oriented towards the dental assistant, enhancing the detection of auxiliary actions during treatment. In some embodiments, the system is further comprising a microphone integrated into the dental chair to capture audio, which is analyzed to complement the video analysis. In some embodiments, the progress display mechanism is an LED or OLED screen capable of showing high-definition graphics and text. In some embodiments, the system is further including a user interface on the display that allows the dental patient to interact with the system, such as by requesting more information about the current treatment step. In some embodiments, the progress display mechanism also shows an estimated time remaining for the current dental procedure step. In some embodiments, the system is further comprising a tactile feedback system integrated into the chair that vibrates to alert the patient at the completion of each treatment step.

In some embodiments, the computerized vision analysis components are configured to use machine learning algorithms to improve the accuracy of stage detection over time. In some embodiments, the multiple cameras include a panoramic camera providing a 180 or 270 or 360-degree view of the treatment area. In some embodiments, the progress display mechanism generates personalized messages to the patient, such as encouragement or educational tips related to dental health. In some embodiments, the system is further including an adjustable lighting system controlled based on the stage of the dental procedure as determined by the computerized vision analysis. In some embodiments, the display includes multi-lingual support to cater to patients who speak different languages.

In some embodiments, the computerized vision analysis components are capable of recognizing and interpreting gestures made by the dental staff. In some embodiments, the system is further comprising a data storage unit to record all video and analysis data for future review or legal documentation. In some embodiments, the system is further including a sub-system to automatically adjust the chair position based on the treatment stage detected. In some embodiments, the computerized vision analysis components are configured to detect emergency situations and alert the dental staff automatically.

In some embodiments, the system is further including a feedback sub-system that allows the patient to rate their experience and comfort level in real-time during the dental procedure. In some embodiments, the multiple cameras are equipped with infrared capabilities for low-light imaging during specific treatment stages. In some embodiments, the system is further comprising a wireless communication module to send real-time updates about the treatment progress to the patient's healthcare provider and/or to family member or companions who may be remote or may be sitting in the waiting room. In some embodiments, the display mechanism is configured to show a visual representation of the patient's mouth that highlights the area currently being treated. In some embodiments, the system is further including an integrated sub-system to dispense anxiety-reducing aromas or scented agents or aromatic agents or aromatherapeutic agents, during specific stages of the dental treatment, or in response to a detection that a particular stage has been reached or was completed. In some embodiments, the display mechanism can be adjusted in its angle and height for optimal visibility by the patient.

In some embodiments, the system is further including the capability to synchronize with a dental practice management software to update patient records in real-time, based on actual treatment progress and at a stage/step granularity; such that, for example, as multi-step dental crown procedure is performed, the Medical Chart/Dental Chart of the patient is gradually and automatically updated during the treatment procedure, by adding the message "Old filling was removed at 10:15 am", and then "antibiotics were inserted at 10:22 am", and then "new filling was inserted at 10:34 am", and so forth.

In some embodiments, the system is further including the capability to detect and record the usage of specific dental tools during the procedure, enhancing the accuracy of the treatment documentation. In some embodiments, the system is further comprising environmental sensors to monitor and adjust the temperature and humidity of the immediate surroundings based on the detected stage of the dental procedure.

Some embodiments may provide or may include one or more of the following features: (1) Virtual Reality Integration: Equip the chair with a VR headset to distract patients during procedures by showing calming scenes or entertainment, potentially reducing anxiety and discomfort. (2) Biometric Monitoring: Integrate sensors to monitor patient vital signs such as heart rate, blood pressure, and oxygen saturation during the dental procedure, ensuring patient safety. (3) Automated Anesthetic Delivery: Include a system that automatically administers localized anesthesia based on the pain level detected through biometric sensors or patient feedback. (4) Personalized Lighting Control: Allow patients to control the color and intensity of the lighting in the treatment room via the chair's interface, helping them feel more comfortable and in control. (5) Haptic Feedback System: Integrate a system that provides gentle vibrations or movements in the chair to help reduce patient anxiety or to signal different stages of the treatment. (6) Adjustable Transparency Display: Implement a display that can switch between transparency and opacity, allowing patients to view their surroundings or receive privacy as needed. (7) Noise-Cancelling Technology: Incorporate noise-cancelling capabilities within the chair to reduce the sound of dental tools, which can be a major source of anxiety for patients. (8) Posture Adjustment Alerts: Use sensors to monitor and alert about the patient's posture during treatment to ensure optimal positioning for both patient comfort and treatment accessibility. (9) Smart Tool Docking Stations: Equip the chair with magnetic docking stations that not only hold dental tools but also sanitize them with UV light when docked. (10) Automated Scent Dispenser: Include a system that releases calming scents like lavender or chamomile during treatments, enhancing patient relaxation. (11) Interactive Patient Education System: Implement a system in the chair's display that can educate patients about their dental health, the procedures being performed, and proper oral hygiene practices. (12) Gesture Control Interface: Allow patients to control chair settings such as recline angle, display content, and lighting using simple hand gestures. (13) Emergency Alert System: Equip the chair with an emergency button or system that the patient can easily activate if they feel undue discomfort or a medical issue arises. (14) Personal Device Integration: Provide a system that allows patients to connect their personal devices for playing their own music or videos, charging their devices, or even mirroring their screens on the chair's display.

Some embodiments may include or provide some or all of the following innovative features or functionalities or components.

Feature 1, Virtual Reality Integration: Equip the dental chair with an integrated virtual reality (VR) headset to immerse patients in calming or entertaining virtual environments during dental procedures. This system could offer various scenarios, such as a peaceful beach, a serene forest, or even a favorite movie or game. The VR experience helps distract patients from the dental procedure, potentially reducing anxiety and the perception of pain. The headset would be adjustable to fit different head sizes and designed for easy sanitization between uses.

Feature 2, Biometric Monitoring: Integrate sensors into the dental chair to continuously monitor the patient's vital signs, such as heart rate, blood pressure, and oxygen saturation. This real-time health data can be crucial for monitoring stress levels and overall health during dental treatments, providing immediate feedback to the dental staff. Alerts can be set up to notify the staff if any readings fall outside normal ranges, ensuring patient safety and allowing for timely interventions.

Feature 3, Automated Anesthetic Delivery: Incorporate a system that automatically administers localized anesthesia based on detected pain levels through biometric sensors or patient input. This feature would use algorithms to calculate the necessary dosage and timing of anesthesia delivery, making the process more efficient and comfortable for the patient. The system could also record dosage and timing data, helping to refine future treatments.

Feature 4, Personalized Lighting Control: Allow patients to personalize the lighting settings in the treatment room using a control panel on the chair or through voice commands. Patients could choose the color and intensity of the lights, creating a soothing environment that can help reduce anxiety. This feature would use LED lighting for a range of color settings and include presets for different moods or treatments.

Feature 5, Haptic Feedback System: This system would integrate gentle vibrations or movements into the chair to communicate with the patient or to soothe them. For instance, the chair could provide a reassuring pulse to indicate that everything is proceeding smoothly or use rhythmic vibrations to help relax the patient. The intensity and pattern of the feedback could be adjustable according to patient preferences or specific treatment needs.

Feature 6, Adjustable Transparency Display: Implement a smart glass panel in front of the patient that can switch between being transparent and opaque. When opaque, it could display information about the treatment, educational content, or entertainment. When transparent, it would allow patients to maintain visual contact with their surroundings and the dental staff, helping them feel less isolated.

Feature 7, Noise-Cancelling components: Equip the chair with built-in passive and active noise-cancelling components to reduce the sound of dental tools, which can be distressing to patients. This could be achieved through noise-cancelling headphones or speakers integrated into the headrest of the chair, playing either soothing music or white noise to mask tool sounds.

Feature 8, Posture Adjustment Alerts: Sensors in the chair would monitor the patient's posture to ensure they remain in the optimal position for treatment. Alerts would be sent to both the patient and the dentist if adjustments are needed, helping to prevent discomfort and ensuring the dentist has the best access for treatment.

Feature 9, Smart Tool Docking Stations: These magnetic docking stations on the chair would not only securely hold dental tools but also automatically sanitize them with UV light when docked. This feature helps maintain hygiene effortlessly and ensures tools are always ready for use.

Feature 10, Automated Scent (odor agent) Dispenser: Integrate a system that releases calming scents, such as lavender or chamomile, during treatments. This could be controlled by the patient or set to activate during specific stages of treatment, providing a more relaxing atmosphere.

Feature 11, Interactive Patient Education System: The chair's display could offer interactive content that educates patients about their dental health, the specific procedures being performed, and proper oral hygiene practices. This feature would be customizable by the dentist to provide relevant information and could include videos, diagrams, and interactive Q&A sessions.

Feature 12, Gesture Control Interface: Allow patients to control various features of the chair, such as the position, display content, and personal device connections, using simple hand gestures. This system would use sensors to detect and interpret patient gestures, making the chair more accessible and reducing the need for physical contact with controls.

Feature 13, Emergency Alert System: An easily accessible emergency button or system would be integrated into the chair, allowing patients to alert dental staff if they experience undue discomfort or a medical issue. This system ensures that patients can receive immediate assistance when needed.

Feature 14, Personal Device Integration: Provide connectivity options for patients to link their personal devices with the chair's system. This would allow them to play their own music or videos, charge their devices, or even mirror device screens on the chair's display. This feature makes the dental experience more enjoyable and personalized.

Some embodiments provide an innovative smart dental treatment chair system designed to enhance the patient experience during dental procedures through the integration of artificial intelligence (AI) and advanced computerized vision. This comprehensive system not only aims to monitor real-time progress of dental treatments but also addresses several common patient concerns such as anxiety, lack of communication, and the need for comfort and reassurance during dental procedures.

The system includes a dental treatment chair equipped with multiple high-tech features including a range of cameras, computerized vision units, a progress display unit, and a multitude of sensors and actuators designed to improve the functionality of the dental chair and enhance patient comfort.

Some embodiments may include, for example, the following features or components:

Feature A, Multi-Camera Setup: The chair includes multiple strategically placed cameras, each serving a specific purpose. These include cameras oriented towards the dentist, the dental assistant, the patient's face, and the overall dental office. This setup not only helps in monitoring the treatment from various angles but also assists in analyzing the interactions between the dentist, the assistant, and the patient.

Feature B, Computerized Vision and Analysis: Utilizing the video feeds from these cameras, the computerized vision units employ advanced algorithms to analyze real-time footage. This analysis helps in identifying which stage of the treatment is being performed. It detects actions like the use of dental tools, the application of materials, and even the positioning of protective equipment like X-ray shields.

Feature C, Progress Display and Interaction: Central to enhancing the patient's experience is the progress display unit, which shows a dynamic progress bar and other relevant information about the ongoing treatment. This not only keeps the patient informed but also reduces anxiety by showing how much of the treatment has been completed and what steps are upcoming.

Feature D, Speech Recognition and Large Language Models (LLM): Speech-to-text technology captures and transcribes the ongoing conversation in the treatment room, which is then analyzed by LLMs to extract and interpret procedural data. This allows the system to update the progress bar accurately and provide textual updates on the display unit about the current phase of the treatment.

Feature E, Adaptive Components: The chair features several adaptive components that respond to the real-time data gathered from the cameras and the computerized analysis. For instance, swiveling and pivoting units adjust the cameras automatically to focus on relevant areas or individuals as needed. This adaptive technology ensures comprehensive monitoring and facilitates a seamless flow of information.

Feature F, Patient Comfort Features: Recognizing the need for physical comfort, the chair includes features like adjustable armrests and a seat that integrates various functionalities such as vibration or movement, tailored to soothe and relax the patient during the treatment.

Feature G, Language and Accessibility Options: To cater to a diverse patient base, the system incorporates features that overcome language barriers and enhance accessibility. This includes multilingual support on the display units and features designed to assist patients and dentists with disabilities, ensuring that everyone has access to clear and understandable treatment information.

Feature H, Automated Emergency Response: Leveraging the system's comprehensive monitoring capabilities, automatic alerts can be triggered in response to detected emergencies or anomalies during the treatment, ensuring swift response times and increasing overall safety.

Feature I, Integration with Dental Management Systems: The chair is designed to integrate seamlessly with existing dental practice management systems. This integration allows for real-time updating of patient records with data on the treatment progress and any other relevant observations noted during the procedure.

Feature J, Enhanced Patient Communication and Comfort: By providing real-time updates and visual progress indicators, the system helps mitigate feelings of anxiety and helplessness that many patients experience during dental treatments. The ability to understand exactly what is happening and what to expect next empowers patients and makes the dental experience less daunting.

Feature K, Increased Efficiency for Dental Professionals: Dentists and dental assistants benefit from the system's ability to automate many routine monitoring tasks. This frees them to focus more on the technical aspects of dental care, improving the overall efficiency of treatment procedures.

Feature L, Improved Treatment Accuracy: With the aid of AI and computerized vision, the system enhances the accuracy of treatment by ensuring that each step is correctly identified and monitored. This not only aids in adhering to treatment protocols but also helps in maintaining high standards of dental care.

Feature M, Customizable and Scalable: The modular nature of the system's components allows for easy customization to fit different dental office setups and patient needs. Additionally, the system's design is scalable, suitable for single-practitioner offices as well as larger dental clinics.

Some embodiments thus provide a forward-thinking solution that leverages modern technology to enhance dental treatment processes. By integrating AI with practical dental operations, it promises to transform the dental care experience for patients and practitioners alike, making it more efficient, comfortable, and safe.

Some embodiments may include or provide the following features or functionalities.

Functionality 1, Integrated Diagnostic Tools: Equip the dental chair with built-in diagnostic modules such as an intraoral scanner and a digital X-ray system. These tools can automatically deploy and retract from the chair and provide real-time imaging and diagnostic data directly to the dentist's monitor. This integration streamlines the diagnostic process, reduces the need for multiple pieces of equipment, and allows for immediate assessment and planning of treatment.

Functionality 2, AI-Powered Treatment Suggestions: Implement an AI system that analyzes the collected diagnostic data to suggest treatment options. This feature uses historical data and machine learning algorithms to propose the most effective treatment plans based on similar cases. It could also provide predictive analytics for future dental issues, helping in preventive care and patient education.

Functionality 3, Automatic Tool Sterilization: Incorporate an automatic sterilization module within the chair's structure where dental tools are sterilized using UV-C light or steam after each use. This feature ensures that all tools are disinfected without requiring manual handling, enhancing safety and efficiency.

Functionality 4, Customizable Comfort Settings: Allow patients to customize their seating experience by adjusting various aspects of the chair such as temperature control, seat cushion firmness, and even the texture of the chair surface. These settings could be saved under the patient's profile for quick setup in future visits.

Functionality 5, Augmented Reality (AR) Display: Integrate an AR system that overlays detailed 3D images of the patient's dental scans over their actual mouth. This technology can be used by dentists to explain the procedural details and expected outcomes to patients more vividly, enhancing understanding and consent.

Functionality 6, Sensory Deprivation Mode: Equip the chair with noise-canceling headphones and a blackout visor that together create a sensory deprivation environment. This can be particularly useful for anxious patients as it helps to block out the sights and sounds of the dental procedure, providing a calming effect.

Functionality 7, Dynamic Pressure Adjustment: Incorporate sensors that detect pressure points and automatically adjust the chair's cushions to redistribute the patient's weight. This helps prevent discomfort during long procedures, ensuring the patient remains comfortable throughout their treatment.

Functionality 8, Voice-Controlled Interface: Implement a voice recognition system that allows both the dentist and the patient to control various functions of the chair and the room, such as adjusting the chair position, controlling the display screens, or even adjusting room lighting and audio.

Functionality 9, Health Monitoring Wristbands: Provide wristbands that monitor the patient's vital signs and stress levels throughout the dental procedure. This data can be used to adjust the treatment dynamically, ensuring the patient's comfort and safety by moderating the pace of the procedure or even pausing it if stress levels become too high.

Functionality 10, Tele-dentistry Capabilities: Equip the chair with built-in cameras and microphones that facilitate real-time video consultations with specialists. This feature can be used to get second opinions, discuss complex cases, or conduct follow-up appointments virtually.

Functionality 11, Interactive Patient Feedback System: Integrate a tablet or touchscreen interface that allows patients to provide immediate feedback on their experience, suggest improvements, and even schedule follow-up appointments. This direct feedback mechanism can help dental practices quickly adjust their procedures and improve patient satisfaction.

Functionality 12, Ergonomic Support Robotics: Attach robotic arms to the chair that can assist in holding tools, suction devices, or other necessary equipment during the procedure. This feature reduces the physical strain on the dentist and the assistant, allowing for more precise and less invasive treatments.

Functionality 13, Automated Medication Dispenser: Include a built-in dispenser that can provide pre-procedure medications or pain relievers as prescribed by the dentist. This automated system ensures correct dosing and timing, improving the efficacy of the medication and patient comfort.

Functionality 14, Multi-Sensory Stimulation System: Integrate systems that can emit calming scents and soothing sounds while also providing gentle visual stimulation using ambient lighting. This multi-sensory approach can significantly enhance patient relaxation and reduce anxiety during procedures.

Functionality 15, Real-time Educational Content Display: Offer real-time educational content about the dental procedures being performed, displayed on screens visible to the patient. This feature can demystify the treatment process, reduce anxiety, and enhance patient knowledge and trust.

Functionality 16, Post-Procedure Care Instructions and Notifications: After a procedure, automatically generate personalized care instructions based on the specific treatments received, which can be printed or sent digitally to the patient. Additionally, integrate a system that sends follow-up reminders and check-in notifications to ensure proper post-procedure care.

Some embodiments may provide or include the following features or components that are surprising or non-obvious or counter-intuitive.

Feature 01, Multiple Orientation-Specific Cameras: Typically, dental chairs might feature a camera for basic recording or monitoring purposes. The idea of integrating multiple cameras each dedicated to capturing specific orientations-dentist, assistant, patient's face, and overall office—is innovative. This setup allows for a comprehensive monitoring system that not only captures every angle of the dental procedure but also the interactions between the dentist, assistant, and patient. Such a multi-perspective monitoring system is crucial for enhancing communication and treatment precision but isn't typically expected in a dental setting where space and simplicity have traditionally been prioritized.

Feature 02, Real-time Progress Display: Providing real-time progress updates via a display visible to the patient during the dental treatment is both surprising and revolutionary. Typically, patients are not informed in real-time about the progress of their treatment due to the complexity of dental procedures and the focus required by dental professionals. By integrating a system that visually represents the treatment's progression, the invention significantly enhances patient experience by reducing anxiety and increasing transparency, which is not a common practice in dental treatments.

Feature 03, Speech-to-Text and LLM Analysis: Utilizing speech-to-text technology combined with Large Language Models (LLMs) to analyze and interpret conversations in the dental office is highly innovative. Typically, any conversation during a dental procedure is not captured for procedural analysis. Here, speech is converted into text and analyzed to determine and update the treatment stages, which is a sophisticated use of AI technology uncommon in everyday dental practice, aiming to enhance the precision and communication of the treatment progression.

Feature 04, Swiveling and Pivoting Cameras Controlled by AI: The use of AI to control the movement of cameras based on the phase of treatment or specific needs during a procedure is highly non-obvious. In traditional setups, cameras, if present, are manually adjusted. This autonomous adjustment not only saves time but also ensures that the best possible angles are always being captured without requiring manual intervention, enhancing procedural efficiency and documentation.

Feature 05, Automatic Adjustment of Chair Features: Chairs that automatically adjust features like lighting, armrests, or even positioning based on the stage of the procedure or the patient's biometric feedback are unexpected. Typically, such adjustments require manual input either from the patient or the dental staff. This proactive adjustment feature uses real-time data to enhance patient comfort and procedure efficacy, which is a novel approach in patient care.

Feature 06, Integrated Diagnostic Tools Within the Chair: Embedding diagnostic tools such as X-rays and scanners directly within the dental chair goes against the conventional design of dental equipment being separate from the chair. This integration allows for seamless transition between diagnosis and treatment, reducing procedure times and improving patient comfort by minimizing the need to move between different stations.

Feature 07, Real-time Automated Sterilization of Tools: The concept of having an in-built system that sterilizes tools in real-time within the chair's structure is quite innovative. Traditionally, sterilization occurs away from the chair in a designated area and involves significant manual handling. This feature minimizes contamination risk and increases efficiency, which is especially critical in a high-sterility environment like dentistry.

Feature 08, AI-Powered Treatment Suggestions: The use of AI to analyze diagnostic data and suggest treatment plans during the dental procedure is surprising. In traditional settings, treatment plans are determined based on the dentist's experience and knowledge without real-time computational support. This feature brings a data-driven approach to dental treatment, potentially increasing the accuracy and personalized care in dental procedures.

Feature 09, Sensory Deprivation Mode: Implementing a mode that can selectively block out sensory input (sound, sight) to relax the patient is counterintuitive in a medical setting where patient awareness is typically prioritized. This feature can significantly ease patient anxiety and transform the dental visit into a less daunting experience, which is especially beneficial for patients with phobias or severe anxiety.

Feature 10, Feedback System for Immediate Patient Input: A system that allows patients to provide feedback during the procedure is unusual since feedback mechanisms are typically post-procedure through surveys. This real-time input can guide the dental staff to adjust their approach immediately, enhancing patient satisfaction and care quality dynamically.

Feature 11, Customizable Environmental Settings Controlled by the Patient: Allowing patients to control environmental settings such as room temperature, chair heating, or even multimedia content during a dental procedure is not traditionally offered. This level of control empowers patients, making them feel more comfortable and involved in their treatment process.

Feature 12, Automated Anesthetic Delivery Based on Biometric Feedback: An anesthetic system that automatically administers pain management based on real-time biometric feedback is a groundbreaking feature. Typically, anesthetics are administered at predetermined stages of a procedure. This automated, responsive system ensures optimal patient comfort without overt reliance on manual monitoring and adjustments by dental staff.

Feature 13, Post-Procedure Care Instructions and Notifications: Automatically generating personalized post-procedure care instructions and follow-up notifications based on the specific treatments received is an innovative approach that extends the care continuum beyond the dental office. Traditionally, post-care instructions are generic and manually conveyed, which can lead to misunderstandings or non-compliance.

Feature 14, Automated Scent Dispenser: Incorporating a system that can release calming or invigorating scents based on the stage of the dental procedure or the patient's stress levels is quite novel. Traditional dental offices might use static air fresheners, but an automated system that adjusts the scent based on real-time conditions is not typical. This feature leverages olfactory stimulation to reduce patient anxiety or even to invigorate them post-procedure, enhancing the overall patient experience and making the environment more pleasant and less clinical.

Feature 15, Gesture-Based Control System: Implementing a gesture control system that allows patients and dental staff to interact with the chair's features or office equipment without physical contact is highly innovative. In traditional setups, most interactions would require manual adjustments or verbal commands. This feature is particularly valuable in maintaining sterility as it reduces the need to touch surfaces during treatment. It also enhances accessibility, allowing patients with limited mobility to easily make adjustments for comfort or communicate their needs.

Feature 16, Personal Health Record Integration: Integrating the dental chair with real-time access to patients' electronic health records is an advanced feature. Typically, dental practices have separate systems for health records that are not actively linked to the operational tools used during dental procedures. By enabling real-time data syncing, the dentist can access comprehensive health information, which can inform treatment decisions, particularly in emergencies or for patients with complex medical histories.

Feature 17, Localized Climate Control: Equipping the chair with a system to control the microclimate around the patient, including temperature, humidity, and even airflow, is unexpected. Unlike traditional climate control which is general and often static, this localized control allows for adjustments that specifically cater to the patient's comfort, potentially improving their tolerance for longer procedures and enhancing their overall experience.

Feature 18, Predictive Maintenance System: Incorporating a predictive maintenance system into the dental chair that uses sensors to monitor the health of the chair and its components is surprisingly technical. Traditional chairs require routine checks that do not predict when a part might fail. This system can alert staff to potential issues before they occur, reducing downtime and maintenance costs, and ensuring that the chair is always operational when needed.

Feature 19, Dynamic Audio Environment Control: Implementing a dynamic audio system that adjusts the sound environment based on the procedure being performed or the patient's preferences is innovative. This could include not only music or white noise but also soundscapes that change in real-time, for instance, becoming more soothing if the patient's stress levels rise, detected through biometric sensors.

Feature 20, Real-Time Language Translation: A real-time language translation feature to automatically translate conversations between the dentist and a patient who speak different languages is a novel idea. While some medical facilities have access to translation services, having this capability integrated directly into the chair's interface would streamline communication and enhance the patient's understanding and comfort during procedures.

Feature 21, Flexible Display Arms: Adding flexible, retractable display arms that can be positioned according to the needs of the procedure or the preference of the patient is a step beyond traditional fixed-position monitors. These arms could enhance the dentist's ability to show detailed images or videos to the patient about their dental health or treatment details, improving communication and patient education.

Feature 22, Virtual Assistant Integration: Integrating a virtual assistant into the dental chair that can respond to voice commands to control various aspects of the chair, provide reminders for the dentist about treatment steps, or even manage scheduling and patient follow-ups during the procedure is unexpected. This assistant would use AI to streamline operations and reduce the cognitive load on dental staff, allowing them to focus more on patient care.

Some embodiments may provide some or all of the following benefits and/or advantageous.

Advantage 1, Enhanced Patient Comfort: The chair's ability to adjust settings automatically, such as temperature and seat cushion firmness, caters to personal comfort preferences, ensuring patients remain relaxed throughout their procedures. This level of personalization can significantly reduce anxiety and discomfort, making dental visits less daunting and more pleasant. Features like the sensory deprivation mode can also help patients who experience severe anxiety by creating a calming environment that distracts from the procedure itself.

Advantage 2, Increased Treatment Efficiency: With multiple cameras providing real-time feedback and AI-driven tools suggesting optimal treatment approaches, dentists can perform procedures more efficiently. This technology reduces the time needed for diagnosis and treatment planning, allowing more patients to be seen in a day without compromising the quality of care, ultimately increasing practice productivity.

Advantage 3, Improved Diagnostic Accuracy: Integrated diagnostic tools within the chair, such as intraoral scanners and digital X-rays, provide high-resolution images that are instantly available. This immediate access to detailed visuals aids in making more accurate diagnoses and developing effective treatment plans, enhancing overall patient outcomes.

Advantage 4, Better Communication: The real-time progress display and language translation features ensure that communication barriers between the dentist and patients are minimized. Patients are kept informed about the status of their treatment, which helps build trust and understanding. For patients and staff who speak different languages, real-time translation can prevent misunderstandings and ensure clear communication.

Advantage 5, Enhanced Safety: Real-time monitoring of the patient's vital signs and stress levels through integrated sensors can alert dental staff to any potential health issues that may arise during a procedure, enabling immediate response. This proactive approach to patient monitoring greatly enhances safety during dental treatments.

Advantage 6, Streamlined Workflow: Gesture-based controls and voice-activated commands allow dental staff to interact with the chair and other connected systems without physical contact, maintaining sterility and reducing the need to manually adjust settings or equipment. This helps keep the workflow smooth and uninterrupted, increasing overall operational efficiency.

Advantage 7, Reduced Physical Strain for Dental Staff: Ergonomic support features, such as robotic arms that can assist in holding and manipulating tools, relieve physical strain on dentists and assistants. This can reduce the incidence of work-related musculoskeletal disorders commonly associated with the profession.

Advantage 8, Customized Patient Education: The ability to display detailed, patient-specific information about dental health and treatments helps in educating patients about their oral health condition and the necessity of proposed treatments. This informed understanding can increase patient compliance with treatment plans and improve long-term dental health outcomes.

Advantage 9, Automated Sterilization Processes: The chair's automated tool sterilization system ensures that all dental instruments are disinfected efficiently and consistently, reducing the risk of infection and streamlining the process of preparing for each patient.

Advantage 10, Environmentally Controlled Treatment Area: Localized climate control within the chair allows for adjustments in temperature and humidity that not only enhance patient comfort but also ensure optimal conditions for certain types of dental treatments, such as those sensitive to temperature and moisture.

Advantage 11, Predictive Maintenance: The predictive maintenance feature of the chair ensures that all components are functioning optimally and alerts staff to potential issues before they cause equipment failure. This proactive maintenance helps avoid unexpected downtime and extends the lifespan of the chair.

Advantage 12, Real-Time Feedback for Immediate Corrections: The integration of cameras and AI analytics allows dental staff to receive immediate feedback on their techniques and the progress of the dental procedure. This capability can lead to immediate corrective actions during the procedure, enhancing treatment effectiveness and reducing the risk of errors.

Advantage 13, Post-Treatment Care and Follow-Up: Automatic generation of personalized care instructions and follow-up reminders after the procedure ensures that patients are well-informed about their post-treatment care. This can lead to better adherence to aftercare instructions and lower complication rates.

Advantage 14, Enhanced Patient Experience: The overall integration of multimedia, environmental controls, and interactive systems transform the dental visit into a more engaging and less stressful experience. Patients can enjoy customized audio or visual content, interact with educational material about their treatment, and feel a greater sense of control and satisfaction with their dental care.

Although portions of the discussion herein relate, for demonstrative purposes, to wired links and/or wired communications, some embodiments of the present invention are not limited in this regard, and may include one or more wired or wireless links, may utilize one or more components of wireless communication, may utilize one or more methods or protocols of wireless communication, or the like. Some embodiments may utilize wired communication and/or wireless communication.

Some embodiments may be implemented by using hardware units, software units, processors, CPUs, DSPs, GPUs, integrated circuits (ICs), logic gates, logic units, memory units, storage units, wireless communication modems or transmitters or receivers or transceivers, cellular transceivers, a power source, input units, output units, Operating System (OS), drivers, applications, and/or other suitable components.

Some embodiments may be implemented by using a special-purpose machine or a specific-purpose that is not a generic computer, or by using a non-generic computer or a non-general computer or machine. Such system or device may utilize or may comprise one or more units or modules that are not part of a "generic computer" and that are not part of a "general purpose computer", for example, cellular transceivers, cellular transmitter, cellular receiver, GPS unit, location-determining unit, accelerometer(s), gyroscope(s), device-orientation detectors or sensors, device-positioning detectors or sensors, or the like.

Some embodiments may be implemented by using code or program code or machine-readable instructions or machine-readable code, which is stored on a non-transitory storage medium or non-transitory storage article (e.g., a CD-ROM, a DVD-ROM, a physical memory unit, a physical storage unit), such that the program or code or instructions, when executed by a processor or a machine or a computer, cause such device to perform a method in accordance with the present invention.

Some embodiments may be utilized with a variety of devices or systems having a touch-screen or a touch-sensitive surface; for example, a smartphone, a cellular phone, a mobile phone, a smart-watch, a tablet, a handheld device, a portable electronic device, a portable gaming device, a portable audio/video player, a Virtual Reality (VR) or Augmented Reality (AR) or Mixed Reality (MR) device or headset or gear, a "kiosk" type device or a vending machine or an Automatic Teller Machine (ATM), a laptop computer, a desktop computer, a vehicular computer or system, a vehicular dashboard, a vehicular touch-screen, or the like.

The system(s) and/or device(s) of some embodiments may optionally comprise, or may be implemented by utilizing suitable hardware components and/or software components; for example, processors, processor cores, Central Processing Units (CPUs), Digital Signal Processors (DSPs), circuits, Integrated Circuits (ICs), controllers, memory units, registers, accumulators, storage units, input units (e.g., touch-screen, keyboard, keypad, stylus, mouse, touchpad, joystick, trackball, microphones), output units (e.g., screen, touch-screen, monitor, display unit, audio speakers), acoustic microphone(s) and/or sensor(s), optical microphone(s) and/or sensor(s), laser or laser-based microphone(s) and/or sensor(s), wired or wireless modems or transceivers or transmitters or receivers, GPS receiver or GPS element or other location-based or location-determining unit or system, network elements (e.g., routers, switches, hubs, antennas), and/or other suitable components and/or modules.

The system(s) and/or devices of some embodiments may optionally be implemented by utilizing co-located components, remote components or modules, "cloud computing" servers or devices or storage, client/server architecture, peer-to-peer architecture, distributed architecture, and/or other suitable architectures or system topologies or network topologies.

In accordance with some embodiments, calculations, operations and/or determinations may be performed locally within a single device, or may be performed by or across multiple devices, or may be performed partially locally and partially remotely (e.g., at a remote server) by optionally utilizing a communication channel to exchange raw data and/or processed data and/or processing results.

Some embodiments may be implemented by using a special-purpose machine or a specific-purpose device that is not a generic computer, or by using a non-generic computer or a non-general computer or machine. Such system or device may utilize or may comprise one or more components or units or modules that are not part of a "generic computer" and that are not part of a "general purpose computer", for example, cellular transceivers, cellular transmitter, cellular receiver, GPS unit, location-determining unit, accelerometer(s), gyroscope(s), device-orientation detectors or sensors, device-positioning detectors or sensors, or the like.

Some embodiments may be implemented as, or by utilizing, an automated method or automated process, or a machine-implemented method or process, or as a semi-automated or partially-automated method or process, or as a set of steps or operations which may be executed or performed by a computer or machine or system or other device.

Some embodiments may be implemented by using code or program code or machine-readable instructions or machine-readable code, which may be stored on a non-transitory storage medium or non-transitory storage article (e.g., a CD-ROM, a DVD-ROM, a physical memory unit, a physical storage unit, a Flash drive), such that the program or code or instructions, when executed by a processor or a machine or a computer, cause such processor or machine or computer to perform a method or process as described herein. Such code or instructions may be or may comprise, for example, one or more of: software, a software module, an application, a program, a subroutine, instructions, an instruction set, computing code, words, values, symbols, strings, variables, source code, compiled code, interpreted code, executable code, static code, dynamic code; including (but not limited to) code or instructions in high-level programming language, low-level programming language, object-oriented programming language, visual programming language, compiled programming language, interpreted programming language, C, C++, C#, Java, JavaScript, SQL, Ruby on Rails, Go, Cobol, Fortran, ActionScript, AJAX, XML, JSON, Lisp, Eiffel, Verilog, Hardware Description Language (HDL), BASIC, Visual BASIC, MATLAB, Pascal, HTML, HTML5, CSS, Dart, Perl, Python, PHP, machine language, machine code, assembly language, or the like.

Discussions herein utilizing terms such as, for example, "processing", "computing", "calculating", "determining", "establishing", "analyzing", "checking", "detecting", "measuring", or the like, may refer to operation(s) and/or process (es) of a processor, a computer, a computing platform, a computing system, or other electronic device or computing device, that may automatically and/or autonomously manipulate and/or transform data represented as physical (e.g., electronic) quantities within registers and/or accumulators and/or memory units and/or storage units into other data or that may perform other suitable operations.

Some embodiments of the present invention may perform steps or operations such as, for example, "determining", "identifying", "comparing", "checking", "querying", "searching", "matching", and/or "analyzing", by utilizing, for example: a pre-defined threshold value to which one or more parameter values may be compared; a comparison between (i) sensed or measured or calculated value(s), and (ii) pre-defined or dynamically-generated threshold value(s) and/or range values and/or upper limit value and/or lower limit value and/or maximum value and/or minimum value; a comparison or matching between sensed or measured or calculated data, and one or more values as stored in a look-up table or a legend table or a list of reference value(s) or a database of reference values or ranges; a comparison or matching or searching process which searches for matches and/or identical results and/or similar results and/or sufficiently-close results (e.g., within a pre-defined threshold level of similarity; such as, within 5 percent above or below a pre-defined threshold value), among multiple values or limits that are stored in a database or look-up table; utilization of one or more equations, formula, weighted formula, and/or other calculation in order to determine similarity or a match between or among parameters or values; utilization of comparator units, lookup tables, threshold values, conditions, conditioning logic, Boolean operator(s) and/or other suitable components and/or operations.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments", "some embodiments", and/or similar terms, may indicate that the embodiment(s) so described may optionally include a particular feature, structure, or characteristic, but not every embodiment necessarily includes the particular feature, structure, or characteristic. Repeated use of the phrase "in one embodiment" does not necessarily refer to the same embodiment, although it may. Repeated use of the phrase "in some embodiments" does not necessarily refer to the same set or group of embodiments, although it may.

As used herein, and unless otherwise specified, the utilization of ordinal adjectives such as "first", "second", "third", "fourth", and so forth, to describe an item or an object, merely indicates that different instances of such like items or objects are being referred to; and does not intend to imply as if the items or objects so described must be in a particular given sequence, either temporally, spatially, in ranking, or in any other ordering manner.

Some embodiments may comprise, or may be implemented by using, an "app" or application which may be downloaded or obtained from an "app store" or "applications store", for free or for a fee, or which may be pre-installed on a computing device or electronic device, or which may be transported to and/or installed on such computing device or electronic device.

Functions, operations, components and/or features described herein with reference to one or more embodiments of the present invention, may be combined with, or may be utilized in combination with, one or more other functions, operations, components and/or features described herein with reference to one or more other embodiments of the present invention. The present invention may comprise any possible combinations, re-arrangements, assembly, re-assembly, or other utilization of some or all of the modules or functions or components that are described herein, even if they are discussed in different locations or different chapters of the above discussion, or even if they are shown across different drawings or multiple drawings.

While certain features of some embodiments have been illustrated and described herein, many modifications, substitutions, changes, and equivalents may occur to those skilled in the art. Accordingly, the claims are intended to cover all such modifications, substitutions, changes, and equivalents.

What is claimed is:

1. A system comprising:

(A) a dental treatment chair, comprising: a seat, and adjustable back-panel, and two movable arm-rests; wherein the dental treatment chair is configured to accommodate therein a dental treatment patient that undergoes a dental procedure at a dentist office by a dentist and a dental assistant;

wherein the dental treatment chair further comprises a movable shelf that is adapted to carry thereon one or more dental tools;

wherein the dental treatment chair comprises, or is connected to, a dental suction device that is configured to suck saliva and fluids from a mouth of said dental treatment patient via an elongated and flexible suction tube;

wherein the dental treatment chair comprises, or is connected to, a dental utility kit that comprises one or more dental tools, which include at least an electric dental drill;

(B1) a first mounting rod, that is integrally connected to said dental treatment chair;

a first camera which is a dentist-oriented camera, that is mounted on said first mounting rod, and is configured to be oriented generally towards an upper body of said dentist, and is configured to capture real-time video of the upper body of said dentist;

(B2) a second mounting rod, that is integrally connected to said dental treatment chair;

a second camera which is a dental assistant oriented camera, that is mounted on said second mounting rod, and is configured to be oriented generally towards an upper body of said dental assistant, and is configured to capture real-time video of the upper body of said dental assistant;

(B3) a third mounting rod, that is integrally connected to said dental treatment chair;

a third camera which is a patient-face oriented camera, that is mounted on said third mounting rod, and is configured to be oriented generally towards a face of said dental treatment patient, and is configured to capture real-time video of the face of said dental treatment patient;

(B4) a fourth mounting rod, that is integrally connected to said dental treatment chair;

a fourth camera which is patient-body oriented camera, that is mounted on said fourth mounting rod, and is configured to be oriented generally towards a torso and legs of said dental treatment patient, and is configured to capture real-time video of the torso and legs of said dental treatment patient;

(B5) a fifth mounting rod, that is integrally connected to said dental treatment chair;

a fifth camera which is an office-oriented camera, that is mounted on said fifth mounting rod, and is configured to be oriented generally towards a field-of-view that comprises a majority of said dentist office that includes said dental treatment chair and said dentist and said dental assistant; wherein the fifth camera is configured to capture real-time video of said majority of said dentist office;

(C) a first Computerized Vision unit, that is implemented using at least a first hardware processor and a first memory unit; wherein the first Computerized Vision unit is configured:

(C1) to receive real-time video from the first camera;

(C2) to receive real-time video from the second camera;

(C3) to receive real-time video from the third camera;

(C4) to receive real-time video from the fourth camera;

(C5) to receive real-time video from the fifth camera;

(C6) to perform computerized vision analysis of the real-time video from the first camera and the real-time video from the second camera and the real-time video from the third camera and the real-time video from the fourth camera and the real-time video from the fifth camera;

(D) a second Computerized Vision unit, that is implemented using at least a second hardware processor and a second memory unit; wherein the second Computerized Vision unit is configured:

(D1) to receive real-time video from the first camera;

(D2) to receive real-time video from the second camera;

(D3) to receive real-time video from the third camera;

(D4) to receive real-time video from the fourth camera;

(D5) to receive real-time video from the fifth camera;

(D6) to perform computerized vision analysis of the real-time video from the first camera and the real-time video from the second camera and the real-time video from the third camera and the real-time video from the fourth camera and the real-time video from the fifth camera;

(D7) based on said computerized vision analysis of (D6), to recognize that a particular step in said dental procedure is occurring, and to generate a Current Step Estimation Signal indicating which step in said dental procedure is estimated to be currently occurring based on computerized vision analysis;

(E) a Progress Display Unit, comprising a digital screen that is that is integrally connected to said dental treatment chair via a sixth mounting rod; wherein said Progress Display Unit is oriented to be in a field-of-view of a said dental treatment patient;

(F) a Current-Step Detector Unit, implemented by utilizing at least a third hardware processor and a third memory unit; wherein the Current-Step Detector Unit is configured, (F1) to determine a current step of the dental procedure, based at least on: (i) the Current Step Estimation Signal that was generated by the second Computerized Vision unit based on computerized vision analysis of real-time video from the first camera and the second camera and the third camera and the fourth camera and the fifth camera, and also, (ii) a multiple-step dental treatment plan that is pre-defined for said dental procedure and that indicates a series of planned consecutive steps of said dental procedure;

(F2) to determine a current Progress Percentage Value, in a range of 0 to 100 percent, indicating an estimated percentage of said dental procedure that has been completed;

(F3) a Progress Bar Generator Unit, to generate a graphical representation of a progress bar corresponding to said current Progress Percentage Value.

2. The system of claim 1, wherein the dental treatment chair further comprises:

(G1) an acoustic microphone configured to capture audio from a vicinity of the dental treatment chair;

(G2) a speech-to-text converter unit, that is implemented by using at least a memory unit and a hardware processor that are configured to convert captured audio from said acoustic microphone into a textual transcript of speech uttered in the vicinity of the dental treatment chair;

(G3) a Large Language Model (LLM) Unit, implemented by utilizing at least a fourth hardware processor and a fourth memory unit, wherein the LLM Unit is configured to receive as inputs: (i) said textual transcript of speech uttered in the vicinity of the dental treatment chair, and also (ii) a textual description of said multiple-step dental treatment plan, and also (iii) a pre-defined title of the dental procedure that is being performed, wherein the LLM Unit is configured, via a pre-defined LLM prompt, to automatically generate a textual output that indicates which particular step of the dental treatment plan is currently being performed, wherein the textual output that is generated by the LLM Unit, that indicates which particular step of the dental treatment plan is currently being performed, is utilized as additional input by the Current-Step Detector Unit for determining the current step that is currently occurring in the dental procedure.

3. The system of claim 2, further comprising:

(G4) an LLM Dental Pre-Training Unit, configured to specifically train or pre-train the LLM Unit on a body-of-knowledge that comprises: (i) a first list of textual titles of dental procedures, and (ii) a second list of detailed textual descriptions that textually explain each step and all steps of each dental procedure that is on the first list.

* * * * *